(12) United States Patent
Denham et al.

(10) Patent No.: US 8,118,836 B2
(45) Date of Patent: Feb. 21, 2012

(54) METHOD AND APPARATUS FOR COUPLING SOFT TISSUE TO A BONE

(75) Inventors: Gregory J. Denham, Warsaw, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 628 days.

(21) Appl. No.: 12/196,410

(22) Filed: Aug. 22, 2008

(65) Prior Publication Data

US 2008/0312689 A1 Dec. 18, 2008

Related U.S. Application Data

(63) Continuation-in-part of application No. 11/541,506, filed on Sep. 29, 2006, now Pat. No. 7,601,165, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, and a continuation-in-part of application No. 11/347,661, filed on Feb. 3, 2006, now Pat. No. 7,749,250, and a continuation-in-part of application No. 11/347,662, filed on Feb. 3, 2006, now abandoned.

(51) Int. Cl.
*A61B 17/04* (2006.01)

(52) U.S. Cl. .................................. 606/232; 606/228
(58) Field of Classification Search ............... 623/13.14, 623/23.72; 606/228, 232, 139, 148
See application file for complete search history.

(56) References Cited

U.S. PATENT DOCUMENTS

| 26,501 A | 10/1859 | Kendrick et al. |
| 65,499 A | 6/1867 | Miller |
| 126,366 A | 4/1872 | Wills |
| 233,475 A | 10/1880 | Cook et al. |
| 261,501 A | 7/1882 | Vandermark |

(Continued)

FOREIGN PATENT DOCUMENTS

AU 4957264 3/1966

(Continued)

OTHER PUBLICATIONS

"EZ Loc Femoral Fixation Device," copyright 2005 Arthrotek, Inc. (8 sheets).

(Continued)

*Primary Examiner* — Darwin Erezo
*Assistant Examiner* — Alexander Orkin
(74) *Attorney, Agent, or Firm* — Harness, Dickey

(57) ABSTRACT

A method and apparatus for coupling a soft tissue implant into a locking cavity formed within a bone is disclosed. The apparatus includes a member to pull the soft tissue implant into a femoral tunnel. The member includes a suture having first and second ends which are passed through first and second openings associated with the longitudinal passage to form a pair of loops. A collapsible tube is positioned about the suture. Application of tension onto the suture construction causes retraction of the soft tissue implant into the femoral tunnel and the collapse of the tube to form an anchor.

29 Claims, 20 Drawing Sheets

U.S. PATENT DOCUMENTS

| | | |
|---|---|---|
| 268,407 A | 12/1882 | Hughes |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,867 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |

| | | | | | |
|---|---|---|---|---|---|
| 4,263,913 A | 4/1981 | Malmin | 4,744,793 A | 5/1988 | Parr et al. |
| 4,265,246 A | 5/1981 | Barry | 4,750,492 A | 6/1988 | Jacobs |
| 4,273,117 A | 6/1981 | Neuhauser et al. | 4,760,843 A | 8/1988 | Fischer et al. |
| 4,275,717 A | 6/1981 | Bolesky | 4,760,844 A | 8/1988 | Kyle |
| 4,287,807 A | 9/1981 | Pacharis et al. | 4,760,848 A | 8/1988 | Hasson |
| 4,291,698 A | 9/1981 | Fuchs et al. | 4,772,261 A | 9/1988 | Von Hoff et al. |
| 4,301,551 A | 11/1981 | Dore et al. | 4,772,286 A | 9/1988 | Goble et al. |
| 4,312,337 A | 1/1982 | Donohue | 4,773,910 A | 9/1988 | Chen et al. |
| 4,316,469 A | 2/1982 | Kapitanov et al. | 4,775,380 A | 10/1988 | Seedhom et al. |
| 4,326,531 A | 4/1982 | Shimonaka et al. | 4,776,328 A | 10/1988 | Frey et al. |
| 4,345,601 A | 8/1982 | Fukuda | 4,781,190 A | 11/1988 | Lee et al. |
| 4,349,027 A | 9/1982 | DiFrancesco | 4,784,126 A | 11/1988 | Hourahane et al. |
| 4,388,921 A | 6/1983 | Sutter et al. | 4,787,882 A | 11/1988 | Claren et al. |
| 4,400,833 A | 8/1983 | Kurland | 4,790,297 A | 12/1988 | Luque et al. |
| 4,402,445 A | 9/1983 | Green | 4,793,363 A | 12/1988 | Ausherman et al. |
| 4,409,974 A | 10/1983 | Freedland | 4,809,695 A | 3/1989 | Gwathmey et al. |
| 4,438,769 A | 3/1984 | Pratt et al. | 4,813,406 A | 3/1989 | Ogle, II |
| 4,441,489 A | 4/1984 | Evans et al. | 4,823,794 A | 4/1989 | Pierce |
| 4,454,875 A | 6/1984 | Pratt et al. | 4,828,562 A | 5/1989 | Kenna |
| 4,462,395 A | 7/1984 | Johnson | 4,832,026 A | 5/1989 | Jones |
| 4,463,753 A | 8/1984 | Gustilo | 4,834,098 A | 5/1989 | Jones |
| 4,473,102 A | 9/1984 | Ohman et al. | 4,838,282 A | 6/1989 | Strasser et al. |
| 4,484,570 A | 11/1984 | Sutter et al. | 4,841,960 A | 6/1989 | Garner |
| 4,489,446 A | 12/1984 | Reed | 4,851,005 A | 7/1989 | Hunt et al. |
| 4,493,323 A | 1/1985 | Albright et al. | 4,858,608 A | 8/1989 | McQuilkin et al. |
| 4,496,468 A | 1/1985 | House et al. | 4,860,513 A | 8/1989 | Whitman |
| 4,505,274 A | 3/1985 | Speelman | 4,863,383 A | 9/1989 | Grafelmann et al. |
| 4,509,516 A | 4/1985 | Richmond | 4,870,957 A | 10/1989 | Goble et al. |
| 4,531,522 A | 7/1985 | Bedi et al. | 4,873,976 A | 10/1989 | Schreiber |
| 4,532,926 A | 8/1985 | O'Holla | 4,887,601 A | 12/1989 | Richards |
| 4,534,350 A | 8/1985 | Golden et al. | 4,890,615 A | 1/1990 | Caspari et al. |
| 4,535,764 A | 8/1985 | Ebert | 4,893,619 A | 1/1990 | Dale et al. |
| 4,537,185 A | 8/1985 | Stednitz | 4,893,974 A | 1/1990 | Fischer et al. |
| 4,549,545 A | 10/1985 | Levy | 4,895,148 A | 1/1990 | Bays et al. |
| 4,549,652 A | 10/1985 | Free | 4,896,668 A | 1/1990 | Popoff et al. |
| 4,561,432 A | 12/1985 | Mazor | 4,898,156 A | 2/1990 | Gatturna et al. |
| 4,564,007 A | 1/1986 | Coombs et al. | 4,899,743 A | 2/1990 | Nicholson et al. |
| 4,570,623 A | 2/1986 | Ellison et al. | 4,901,721 A | 2/1990 | Hakki |
| 4,573,844 A | 3/1986 | Smith | 4,923,461 A | 5/1990 | Caspari et al. |
| 4,576,608 A | 3/1986 | Homsy | 4,927,421 A | 5/1990 | Goble et al. |
| 4,584,722 A | 4/1986 | Levy et al. | 4,946,468 A | 8/1990 | Li |
| 4,590,928 A | 5/1986 | Hunt et al. | 4,950,270 A | 8/1990 | Bowman et al. |
| 4,595,007 A | 6/1986 | Mericle | 4,950,285 A | 8/1990 | Wilk |
| 4,596,249 A | 6/1986 | Freda et al. | 4,960,381 A | 10/1990 | Niznick |
| 4,602,635 A | 7/1986 | Mulhollan et al. | 4,961,741 A | 10/1990 | Hayhurst |
| 4,602,636 A | 7/1986 | Noiles | 4,968,315 A | 11/1990 | Gatturna |
| 4,604,997 A | 8/1986 | De Bastiani et al. | 4,968,317 A | 11/1990 | Tormala et al. |
| 4,605,414 A | 8/1986 | Czajka | 4,969,886 A | 11/1990 | Cziffer et al. |
| 4,616,650 A | 10/1986 | Green et al. | 4,976,736 A | 12/1990 | White et al. |
| 4,621,640 A | 11/1986 | Mulhollan et al. | 4,978,350 A | 12/1990 | Wagenknecht et al. |
| 4,624,254 A | 11/1986 | McGarry et al. | 4,979,956 A | 12/1990 | Silvestrini |
| 4,632,100 A | 12/1986 | Somers et al. | 4,983,176 A | 1/1991 | Cushman et al. |
| 4,635,637 A | 1/1987 | Schreiber | 4,988,351 A | 1/1991 | Paulos et al. |
| 4,636,121 A | 1/1987 | Miller | 4,994,074 A | 2/1991 | Bezwada et al. |
| 4,641,652 A | 2/1987 | Hutterer et al. | 4,997,433 A | 3/1991 | Goble et al. |
| 4,649,952 A | 3/1987 | Jobe | 5,002,550 A | 3/1991 | Li |
| 4,653,486 A | 3/1987 | Coker | 5,002,562 A | 3/1991 | Oberlander |
| 4,653,487 A | 3/1987 | Maale | 5,007,921 A | 4/1991 | Brown |
| 4,653,489 A | 3/1987 | Tronzo | 5,030,224 A | 7/1991 | Wright et al. |
| 4,655,777 A | 4/1987 | Dunn et al. | 5,037,422 A | 8/1991 | Hayhurst et al. |
| 4,662,068 A | 5/1987 | Polonsky | 5,041,129 A | 8/1991 | Hayhurst et al. |
| 4,667,662 A | 5/1987 | Titone et al. | 5,046,513 A | 9/1991 | Gatturna et al. |
| 4,667,675 A | 5/1987 | Davis | 5,047,030 A | 9/1991 | Draenert et al. |
| 4,669,473 A | 6/1987 | Richards et al. | 5,053,046 A | 10/1991 | Janese |
| 4,683,895 A | 8/1987 | Pohndorf | 5,053,047 A | 10/1991 | Yoon |
| 4,688,561 A | 8/1987 | Reese | 5,059,201 A | 10/1991 | Asnis |
| 4,690,169 A | 9/1987 | Jobe | 5,059,206 A | 10/1991 | Winters |
| 4,705,040 A | 11/1987 | Mueller et al. | 5,061,277 A | 10/1991 | Carpentier et al. |
| 4,708,132 A | 11/1987 | Silvestrini | 5,062,344 A | 11/1991 | Gerker |
| 4,716,893 A | 1/1988 | Fischer et al. | 5,062,843 A | 11/1991 | Mahony, III |
| 4,719,671 A | 1/1988 | Ito et al. | 5,064,431 A | 11/1991 | Gilbertson et al. |
| 4,719,917 A | 1/1988 | Barrows et al. | 5,074,874 A | 12/1991 | Yoon et al. |
| 4,723,540 A | 2/1988 | Gilmer, Jr. | 5,078,731 A | 1/1992 | Hayhurst |
| 4,724,839 A | 2/1988 | Bedi et al. | 5,078,843 A | 1/1992 | Pratt |
| 4,728,332 A | 3/1988 | Albrektsson et al. | 5,084,050 A | 1/1992 | Draenert et al. |
| 4,738,255 A | 4/1988 | Goble et al. | 5,084,058 A | 1/1992 | Li |
| 4,741,330 A | 5/1988 | Hayhurst | 5,085,661 A | 2/1992 | Moss |
| 4,741,336 A | 5/1988 | Failla et al. | 5,087,263 A | 2/1992 | Li |
| 4,744,353 A | 5/1988 | McFarland | 5,092,866 A | 3/1992 | Breard et al. |

| | | | | | | |
|---|---|---|---|---|---|---|
| 5,098,435 | A | 3/1992 | Stednitz et al. | 5,358,511 A | 10/1994 | Gatturna et al. |
| 5,100,415 | A | 3/1992 | Hayhurst | 5,360,431 A | 11/1994 | Puno et al. |
| 5,100,417 | A | 3/1992 | Cerier et al. | 5,362,294 A | 11/1994 | Seitzinger |
| 5,116,337 | A | 5/1992 | Johnson | 5,364,400 A | 11/1994 | Rego, Jr. et al. |
| 5,116,373 | A | 5/1992 | Jakob et al. | 5,368,599 A | 11/1994 | Hirsch et al. |
| 5,116,375 | A | 5/1992 | Hofmann | 5,370,661 A | 12/1994 | Branch |
| 5,123,913 | A | 6/1992 | Wilk et al. | 5,370,662 A | 12/1994 | Stone et al. |
| 5,123,914 | A | 6/1992 | Cope | 5,372,146 A | 12/1994 | Branch |
| 5,127,785 | A | 7/1992 | Faucher et al. | 5,372,604 A | 12/1994 | Trott |
| 5,129,901 | A | 7/1992 | Decoste | 5,372,821 A | 12/1994 | Badylak et al. |
| 5,129,902 | A | 7/1992 | Goble et al. | 5,374,268 A | 12/1994 | Sander |
| 5,129,904 | A | 7/1992 | Illi et al. | 5,379,492 A | 1/1995 | Glesser |
| 5,129,906 | A | 7/1992 | Ross et al. | 5,383,878 A | 1/1995 | Roger et al. |
| 5,139,499 | A | 8/1992 | Small et al. | 5,383,904 A | 1/1995 | Totakura et al. |
| 5,139,520 | A | 8/1992 | Rosenberg | 5,391,171 A | 2/1995 | Schmieding |
| 5,143,498 | A | 9/1992 | Whitman | 5,391,176 A | 2/1995 | de la Torre |
| 5,147,362 | A | 9/1992 | Goble | 5,393,302 A | 2/1995 | Clark et al. |
| 5,149,329 | A | 9/1992 | Richardson | RE34,871 E | 3/1995 | McGuire et al. |
| 5,152,790 | A | 10/1992 | Rosenberg et al. | 5,397,356 A | 3/1995 | Goble et al. |
| 5,154,189 | A | 10/1992 | Oberlander | 5,403,328 A | 4/1995 | Shallman |
| 5,156,616 | A | 10/1992 | Meadows et al. | 5,403,329 A | 4/1995 | Hinchcliffe |
| 5,163,960 | A | 11/1992 | Bonutti | 5,403,348 A | 4/1995 | Bonutti |
| D331,626 | S | 12/1992 | Hayhurst et al. | 5,417,691 A | 5/1995 | Hayhurst |
| 5,169,400 | A | 12/1992 | Muhling et al. | 5,417,712 A | 5/1995 | Whittaker et al. |
| 5,176,682 | A | 1/1993 | Chow | 5,423,819 A | 6/1995 | Small et al. |
| 5,178,629 | A | 1/1993 | Kammerer | 5,423,823 A | 6/1995 | Schmieding |
| 5,183,458 | A | 2/1993 | Marx | 5,423,860 A | 6/1995 | Lizardi et al. |
| 5,192,282 | A | 3/1993 | Draenert et al. | 5,425,733 A | 6/1995 | Schmieding |
| 5,197,987 | A | 3/1993 | Koch et al. | 5,425,766 A | 6/1995 | Bowald et al. |
| 5,203,784 | A | 4/1993 | Ross et al. | 5,433,751 A | 7/1995 | Christel et al. |
| 5,203,787 | A | 4/1993 | Noblitt et al. | 5,437,680 A | 8/1995 | Yoon |
| 5,207,679 | A | 5/1993 | Li | 5,439,684 A | 8/1995 | Prewett et al. |
| 5,209,753 | A | 5/1993 | Biedermann et al. | 5,441,508 A | 8/1995 | Gazielly et al. |
| 5,209,805 | A | 5/1993 | Spraggins | 5,443,468 A | 8/1995 | Johnson |
| 5,211,647 | A | 5/1993 | Schmieding | 5,443,482 A | 8/1995 | Stone et al. |
| 5,211,650 | A | 5/1993 | Noda | 5,443,483 A | 8/1995 | Kirsch et al. |
| 5,214,987 | A | 6/1993 | Fenton, Sr. | 5,443,509 A | 8/1995 | Boucher et al. |
| 5,219,359 | A | 6/1993 | McQuilkin et al. | 5,445,833 A | 8/1995 | Badylak et al. |
| 5,222,976 | A | 6/1993 | Yoon | 5,447,512 A | 9/1995 | Wilson et al. |
| 5,224,946 | A | 7/1993 | Hayhurst et al. | 5,451,203 A | 9/1995 | Lamb |
| 5,230,699 | A | 7/1993 | Grasinger | 5,454,811 A | 10/1995 | Huebner |
| 5,232,436 | A | 8/1993 | Janevski | 5,456,685 A | 10/1995 | Huebner |
| 5,234,435 | A | 8/1993 | Seagrave, Jr. | 5,456,722 A | 10/1995 | McLeod et al. |
| 5,235,238 | A | 8/1993 | Nomura et al. | 5,458,601 A | 10/1995 | Young, Jr. et al. |
| 5,236,445 | A | 8/1993 | Hayhurst et al. | 5,458,604 A | 10/1995 | Schmieding |
| 5,236,461 | A | 8/1993 | Forte | 5,462,560 A | 10/1995 | Stevens |
| 5,242,447 | A | 9/1993 | Borzone | 5,464,426 A | 11/1995 | Bonutti |
| 5,246,441 | A | 9/1993 | Ross et al. | 5,464,427 A | 11/1995 | Curtis et al. |
| 5,249,899 | A | 10/1993 | Wilson | 5,464,440 A | 11/1995 | Johansson et al. |
| 5,258,015 | A | 11/1993 | Li et al. | 5,466,237 A | 11/1995 | Byrd, III et al. |
| 5,258,016 | A | 11/1993 | DiPoto et al. | 5,467,786 A | 11/1995 | Allen et al. |
| 5,258,040 | A | 11/1993 | Bruchman et al. | 5,470,334 A | 11/1995 | Ross et al. |
| 5,268,001 | A | 12/1993 | Nicholson et al. | 5,470,337 A | 11/1995 | Moss |
| 5,269,160 | A | 12/1993 | Wood | 5,470,338 A | 11/1995 | Whitfield et al. |
| 5,269,783 | A | 12/1993 | Sander | 5,472,452 A | 12/1995 | Trott |
| 5,269,809 | A | 12/1993 | Hayhurst et al. | 5,474,565 A | 12/1995 | Trott |
| 5,281,422 | A | 1/1994 | Badylak et al. | 5,474,568 A | 12/1995 | Scott |
| 5,282,809 | A | 2/1994 | Kammerer et al. | 5,474,572 A | 12/1995 | Hayhurst |
| 5,282,832 | A | 2/1994 | Toso et al. | 5,478,344 A | 12/1995 | Stone et al. |
| 5,282,867 | A | 2/1994 | Mikhail | 5,478,345 A | 12/1995 | Stone et al. |
| 5,285,040 | A | 2/1994 | Brandberg et al. | 5,480,403 A | 1/1996 | Lee et al. |
| 5,290,217 | A | 3/1994 | Campos | 5,480,406 A | 1/1996 | Nolan et al. |
| 5,306,301 | A | 4/1994 | Graf et al. | 5,484,442 A | 1/1996 | Melker et al. |
| 5,312,422 | A | 5/1994 | Trott | 5,486,197 A | 1/1996 | Le et al. |
| 5,312,438 | A | 5/1994 | Johnson | 5,490,750 A | 2/1996 | Gundy |
| 5,318,577 | A | 6/1994 | Li | 5,496,331 A | 3/1996 | Xu et al. |
| 5,318,578 | A | 6/1994 | Hasson | 5,496,348 A | 3/1996 | Bonutti |
| 5,320,115 | A | 6/1994 | Kenna | 5,500,000 A | 3/1996 | Feagin et al. |
| 5,320,626 | A | 6/1994 | Schmieding | 5,505,736 A | 4/1996 | Reimels et al. |
| 5,320,633 | A | 6/1994 | Allen et al. | 5,507,754 A | 4/1996 | Green et al. |
| 5,324,308 | A | 6/1994 | Pierce | 5,520,691 A | 5/1996 | Branch |
| 5,334,204 | A | 8/1994 | Clewett et al. | 5,520,702 A | 5/1996 | Sauer et al. |
| 5,336,229 | A | 8/1994 | Noda | 5,522,817 A | 6/1996 | Sander et al. |
| 5,336,231 | A | 8/1994 | Adair | 5,522,820 A | 6/1996 | Caspari et al. |
| 5,336,240 | A | 8/1994 | Metzler et al. | 5,522,844 A | 6/1996 | Johnson |
| 5,342,369 | A | 8/1994 | Harryman, II | 5,522,845 A | 6/1996 | Wenstrom, Jr. |
| 5,346,462 | A | 9/1994 | Barber | 5,522,846 A | 6/1996 | Bonutti |
| 5,354,298 | A | 10/1994 | Lee et al. | 5,524,946 A | 6/1996 | Thompson |
| 5,356,413 | A | 10/1994 | Martins et al. | 5,527,321 A | 6/1996 | Hinchliffe |

| | | | | | | |
|---|---|---|---|---|---|---|
| 5,527,342 A | 6/1996 | Pietrzak et al. | | 5,707,373 A | 1/1998 | Sevrain et al. |
| 5,527,343 A | 6/1996 | Bonutti | | 5,713,005 A | 1/1998 | Proebsting |
| 5,534,012 A | 7/1996 | Bonutti | | 5,713,904 A | 2/1998 | Errico et al. |
| 5,540,718 A | 7/1996 | Bartlett | | 5,713,905 A | 2/1998 | Goble et al. |
| 5,545,178 A | 8/1996 | Kensey et al. | | 5,713,921 A | 2/1998 | Bonutti |
| 5,545,228 A | 8/1996 | Kambin | | 5,716,359 A | 2/1998 | Ojima et al. |
| 5,549,613 A | 8/1996 | Goble et al. | | 5,716,397 A | 2/1998 | Myers |
| 5,549,617 A | 8/1996 | Green et al. | | 5,718,717 A | 2/1998 | Bonutti |
| 5,549,630 A | 8/1996 | Bonutti | | 5,720,747 A | 2/1998 | Burke |
| 5,549,631 A | 8/1996 | Bonutti | | 5,720,765 A | 2/1998 | Thal |
| 5,562,683 A | 10/1996 | Chan | | 5,720,766 A | 2/1998 | Zang et al. |
| 5,562,685 A | 10/1996 | Mollenauer et al. | | 5,725,549 A | 3/1998 | Lam |
| 5,562,686 A | 10/1996 | Sauer et al. | | 5,725,556 A | 3/1998 | Moser et al. |
| 5,569,269 A | 10/1996 | Hart et al. | | 5,725,581 A | 3/1998 | Brånemark et al. |
| 5,569,305 A | 10/1996 | Bonutti | | 5,725,582 A | 3/1998 | Bevan et al. |
| 5,571,090 A | 11/1996 | Sherts | | 5,726,722 A | 3/1998 | Uehara et al. |
| 5,571,139 A | 11/1996 | Jenkins, Jr. | | 5,728,107 A | 3/1998 | Zlock et al. |
| 5,572,655 A | 11/1996 | Tuljapurkar et al. | | 5,728,109 A | 3/1998 | Schulze et al. |
| 5,573,286 A | 11/1996 | Rogozinski | | 5,728,136 A | 3/1998 | Thal |
| 5,573,542 A | 11/1996 | Stevens | | 5,733,293 A | 3/1998 | Scirica et al. |
| 5,573,548 A | 11/1996 | Nazre et al. | | 5,733,306 A | 3/1998 | Bonutti |
| 5,577,299 A | 11/1996 | Thompson et al. | | 5,733,307 A | 3/1998 | Dinsdale |
| 5,578,057 A | 11/1996 | Wenstrom, Jr. | | 5,735,875 A | 4/1998 | Bonutti et al. |
| 5,584,695 A | 12/1996 | Lal Sachdeva et al. | | 5,741,259 A | 4/1998 | Chan |
| 5,584,835 A | 12/1996 | Greenfield | | 5,741,281 A | 4/1998 | Martin et al. |
| 5,584,836 A | 12/1996 | Ballintyn et al. | | 5,743,912 A | 4/1998 | Lahille et al. |
| 5,584,862 A | 12/1996 | Bonutti | | 5,746,751 A | 5/1998 | Sherts |
| 5,586,986 A | 12/1996 | Hinchliffe | | 5,746,752 A | 5/1998 | Burkhart |
| 5,588,575 A | 12/1996 | Davignon | | 5,746,754 A | 5/1998 | Chan |
| 5,591,180 A | 1/1997 | Hinchliffe | | 5,749,898 A | 5/1998 | Schulze et al. |
| 5,591,181 A | 1/1997 | Stone et al. | | 5,755,729 A | 5/1998 | de la Torre et al. |
| 5,591,207 A | 1/1997 | Coleman | | 5,766,176 A | 6/1998 | Duncan |
| 5,593,407 A | 1/1997 | Reis et al. | | 5,766,250 A | 6/1998 | Chervitz et al. |
| 5,593,425 A | 1/1997 | Bonutti et al. | | 5,769,894 A | 6/1998 | Ferragamo |
| 5,601,557 A | 2/1997 | Hayhurst | | 5,769,899 A | 6/1998 | Schwartz et al. |
| 5,601,559 A | 2/1997 | Melker et al. | | 5,772,673 A | 6/1998 | Cuny et al. |
| 5,601,571 A | 2/1997 | Moss | | 5,776,196 A | 7/1998 | Matsuzaki et al. |
| 5,603,716 A | 2/1997 | Morgan et al. | | 5,782,862 A | 7/1998 | Bonutti |
| 5,607,429 A | 3/1997 | Hayano et al. | | 5,782,864 A | 7/1998 | Lizardi |
| 5,618,290 A | 4/1997 | Toy et al. | | 5,782,866 A | 7/1998 | Wenstrom, Jr. |
| 5,628,756 A | 5/1997 | Barker, Jr. et al. | | 5,785,714 A | 7/1998 | Morgan et al. |
| 5,628,766 A | 5/1997 | Johnson | | 5,792,142 A | 8/1998 | Galitzer |
| 5,630,824 A | 5/1997 | Hart | | 5,792,149 A | 8/1998 | Sherts et al. |
| 5,632,748 A | 5/1997 | Beck, Jr. et al. | | 5,796,127 A | 8/1998 | Hayafuji et al. |
| 5,641,256 A | 6/1997 | Gundy | | 5,797,928 A | 8/1998 | Kogasaka et al. |
| 5,643,266 A | 7/1997 | Li | | 5,800,407 A | 9/1998 | Eldor et al. |
| 5,643,269 A | 7/1997 | Harle et al. | | 5,810,824 A | 9/1998 | Chan |
| 5,643,295 A | 7/1997 | Yoon | | 5,810,848 A | 9/1998 | Hayhurst |
| 5,643,320 A | 7/1997 | Lower et al. | | 5,814,069 A | 9/1998 | Schulze et al. |
| 5,643,321 A | 7/1997 | McDevitt | | 5,814,070 A | 9/1998 | Borzone et al. |
| 5,645,546 A | 7/1997 | Fard | | 5,814,072 A | 9/1998 | Bonutti |
| 5,645,547 A | 7/1997 | Coleman | | 5,814,073 A | 9/1998 | Bonutti |
| 5,645,568 A | 7/1997 | Chervitz et al. | | 5,823,980 A | 10/1998 | Kopfer |
| 5,645,588 A | 7/1997 | Graf et al. | | 5,824,011 A | 10/1998 | Stone et al. |
| 5,647,874 A | 7/1997 | Hayhurst | | 5,843,084 A | 12/1998 | Hart et al. |
| 5,649,959 A | 7/1997 | Hannam et al. | | 5,845,645 A | 12/1998 | Bonutti |
| 5,649,963 A | 7/1997 | McDevitt | | 5,846,254 A | 12/1998 | Schulze et al. |
| 5,658,289 A | 8/1997 | Boucher et al. | | 5,848,983 A | 12/1998 | Basaj et al. |
| 5,658,299 A | 8/1997 | Hart | | 5,860,973 A | 1/1999 | Michelson |
| 5,658,313 A | 8/1997 | Thal | | 5,868,740 A | 2/1999 | LeVeen et al. |
| 5,662,658 A | 9/1997 | Wenstrom, Jr. | | 5,868,789 A | 2/1999 | Huebner |
| 5,662,663 A | 9/1997 | Shallman | | 5,871,484 A | 2/1999 | Spievack et al. |
| 5,665,112 A | 9/1997 | Thal | | 5,871,486 A | 2/1999 | Huebner et al. |
| 5,667,513 A | 9/1997 | Torrie et al. | | 5,871,490 A | 2/1999 | Schulze et al. |
| 5,671,695 A | 9/1997 | Schroeder | | 5,885,294 A | 3/1999 | Pedlick et al. |
| 5,674,224 A | 10/1997 | Howell et al. | | 5,891,168 A | 4/1999 | Thal |
| 5,679,723 A | 10/1997 | Cooper et al. | | 5,893,592 A | 4/1999 | Schulze et al. |
| 5,681,334 A | 10/1997 | Evans et al. | | 5,895,395 A | 4/1999 | Yeung |
| 5,681,352 A | 10/1997 | Clancy, III et al. | | 5,897,564 A | 4/1999 | Schulze et al. |
| 5,683,419 A | 11/1997 | Thal | | 5,897,574 A | 4/1999 | Bonutti |
| 5,688,285 A | 11/1997 | Yamada et al. | | 5,899,902 A | 5/1999 | Brown et al. |
| 5,690,676 A | 11/1997 | DiPoto et al. | | 5,899,938 A | 5/1999 | Sklar et al. |
| 5,690,678 A | 11/1997 | Johnson | | 5,908,421 A | 6/1999 | Beger et al. |
| 5,695,497 A | 12/1997 | Stahelin et al. | | 5,908,436 A | 6/1999 | Cuschieri et al. |
| 5,697,929 A | 12/1997 | Mellinger | | 5,910,148 A | 6/1999 | Reimels et al. |
| 5,699,657 A | 12/1997 | Paulson | | 5,911,721 A | 6/1999 | Nicholson et al. |
| 5,702,397 A | 12/1997 | Goble et al. | | 5,918,604 A | 7/1999 | Whelan |
| 5,702,422 A | 12/1997 | Stone | | 5,921,986 A | 7/1999 | Bonutti |
| 5,702,462 A | 12/1997 | Oberlander | | 5,925,008 A | 7/1999 | Douglas |

| | | |
|---|---|---|
| 5,928,267 A | 7/1999 | Bonutti et al. |
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |
| 5,968,047 A | 10/1999 | Reed |
| 5,976,125 A | 11/1999 | Graham |
| 5,976,127 A | 11/1999 | Lax |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex et al. |
| 5,989,256 A | 11/1999 | Kuslich et al. |
| 5,989,282 A | 11/1999 | Bonutti |
| 5,993,452 A | 11/1999 | Vandewalle |
| 5,997,542 A | 12/1999 | Burke |
| 5,997,552 A | 12/1999 | Person et al. |
| 6,001,100 A | 12/1999 | Sherman et al. |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,053,916 A | 4/2000 | Moore |
| 6,056,752 A | 5/2000 | Roger et al. |
| 6,056,772 A | 5/2000 | Bonutti |
| 6,056,773 A | 5/2000 | Bonutti |
| 6,059,817 A | 5/2000 | Bonutti et al. |
| 6,062,344 A | 5/2000 | Okabe et al. |
| 6,068,648 A | 5/2000 | Cole et al. |
| 6,074,403 A | 6/2000 | Nord |
| 6,077,277 A | 6/2000 | Mollenauer et al. |
| 6,077,292 A | 6/2000 | Bonutti |
| 6,086,591 A | 7/2000 | Bojarski |
| 6,086,592 A | 7/2000 | Rosenberg et al. |
| 6,086,608 A | 7/2000 | Ek et al. |
| 6,096,060 A | 8/2000 | Fitts et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom et al. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,283,973 B1 | 9/2001 | Hubbard et al. |
| 6,283,996 B1 | 9/2001 | Chervitz et al. |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |

| | | |
|---|---|---|
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex et al. |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,066,942 B2 | 6/2006 | Treace |
| 7,066,944 B2 | 6/2006 | Laufer et al. |
| 7,105,010 B2 | 9/2006 | Hart et al. |
| 7,112,221 B2 | 9/2006 | Harris |
| 7,118,583 B2 | 10/2006 | O'Quinn et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,201,722 B2 | 4/2007 | Krueger |
| 7,255,675 B2 | 8/2007 | Gertner et al. |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |

| | | |
|---|---|---|
| 7,306,417 B2 | 12/2007 | Dorstewitz |
| 7,326,222 B2 | 2/2008 | Dreyfuss et al. |
| 7,390,329 B2 | 6/2008 | Westra et al. |
| 7,390,332 B2 | 6/2008 | Selvitelli et al. |
| 7,442,210 B2 | 10/2008 | Segal et al. |
| 7,585,311 B2 | 9/2009 | Green et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,736,379 B2 | 6/2010 | Ewers et al. |
| 7,758,594 B2 | 7/2010 | Lamson et al. |
| 7,776,041 B1 | 8/2010 | Walters |
| 7,819,895 B2 | 10/2010 | Ginn et al. |
| 7,875,058 B2 | 1/2011 | Holmes, Jr. |
| 7,981,140 B2 | 7/2011 | Burkhart |
| 8,062,334 B2 | 11/2011 | Green et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1 | 2/2002 | Sikora et al. |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0044391 A1 | 3/2004 | Porter |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0251208 A1 | 11/2005 | Elmer et al. |
| 2005/0267479 A1 | 12/2005 | Morgan et al. |
| 2005/0267533 A1 | 12/2005 | Gertner |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0030884 A1 | 2/2006 | Yeung et al. |

| | | | |
|---|---|---|---|
| 2006/0030948 A1 | 2/2006 | Manrique et al. | |
| 2006/0036265 A1 | 2/2006 | Dant | |
| 2006/0064126 A1 | 3/2006 | Fallin et al. | |
| 2006/0069334 A1 | 3/2006 | Moskowitz | |
| 2006/0084943 A1 | 4/2006 | Rosenman et al. | |
| 2006/0100627 A1 | 5/2006 | Stone et al. | |
| 2006/0116685 A1 | 6/2006 | Urbanski et al. | |
| 2006/0121084 A1 | 6/2006 | Borden et al. | |
| 2006/0135958 A1 | 6/2006 | Marissen et al. | |
| 2006/0149266 A1 | 7/2006 | Cordasco | |
| 2006/0167481 A1 | 7/2006 | Baker et al. | |
| 2006/0167482 A1 | 7/2006 | Swain et al. | |
| 2006/0178680 A1 | 8/2006 | Nelson et al. | |
| 2006/0189993 A1 | 8/2006 | Stone | |
| 2006/0190042 A1 | 8/2006 | Stone et al. | |
| 2006/0229671 A1 | 10/2006 | Steiner et al. | |
| 2006/0247642 A1 | 11/2006 | Stone et al. | |
| 2006/0253130 A1 | 11/2006 | Wolniewicz | |
| 2006/0271192 A1 | 11/2006 | Olsen et al. | |
| 2006/0280768 A1 | 12/2006 | Hwang et al. | |
| 2006/0282082 A1 | 12/2006 | Fanton et al. | |
| 2006/0282085 A1 | 12/2006 | Stone et al. | |
| 2006/0293709 A1 | 12/2006 | Bojarski et al. | |
| 2007/0005080 A1 | 1/2007 | Wolniewicz et al. | |
| 2007/0016305 A1 | 1/2007 | Chudik | |
| 2007/0055255 A1 | 3/2007 | Siegel | |
| 2007/0060922 A1 | 3/2007 | Dreyfuss | |
| 2007/0067025 A1 | 3/2007 | Schwartz | |
| 2007/0073307 A1 | 3/2007 | Scribner et al. | |
| 2007/0078435 A1 | 4/2007 | Stone et al. | |
| 2007/0083236 A1 | 4/2007 | Sikora et al. | |
| 2007/0093847 A1 | 4/2007 | Scribner et al. | |
| 2007/0142838 A1 | 6/2007 | Jordan | |
| 2007/0185532 A1 | 8/2007 | Stone et al. | |
| 2007/0191849 A1 | 8/2007 | ElAttrache et al. | |
| 2007/0219558 A1 | 9/2007 | Deutsch | |
| 2007/0239209 A1 | 10/2007 | Fallman | |
| 2007/0239275 A1 | 10/2007 | Willobee | |
| 2007/0250163 A1 | 10/2007 | Cassani | |
| 2008/0027446 A1 | 1/2008 | Stone et al. | |
| 2008/0046009 A1 | 2/2008 | Albertorio et al. | |
| 2008/0065114 A1 | 3/2008 | Stone et al. | |
| 2008/0082127 A1 | 4/2008 | Stone et al. | |
| 2008/0082128 A1 | 4/2008 | Stone | |
| 2008/0132753 A1 | 6/2008 | Goddard | |
| 2008/0132932 A1 | 6/2008 | Hoeppner et al. | |
| 2008/0140092 A1 | 6/2008 | Stone et al. | |
| 2008/0140093 A1 | 6/2008 | Stone et al. | |
| 2008/0161852 A1 | 7/2008 | Kaiser et al. | |
| 2008/0188936 A1 | 8/2008 | Ball et al. | |
| 2008/0221527 A1 | 9/2008 | Bradley et al. | |
| 2008/0255613 A1 | 10/2008 | Kaiser et al. | |
| 2008/0262544 A1 | 10/2008 | Burkhart | |
| 2008/0268064 A1 | 10/2008 | Woodell-May | |
| 2008/0269674 A1 | 10/2008 | Stone | |
| 2008/0275477 A1 | 11/2008 | Sterrett et al. | |
| 2009/0054928 A1 | 2/2009 | Denham et al. | |
| 2009/0062854 A1 | 3/2009 | Kaiser et al. | |
| 2009/0082805 A1 | 3/2009 | Kaiser et al. | |
| 2009/0138002 A1 | 5/2009 | Fenton | |
| 2009/0156997 A1 | 6/2009 | Trenhaile | |
| 2009/0177233 A1 | 7/2009 | Malek | |
| 2009/0192468 A1 | 7/2009 | Stone | |
| 2009/0204146 A1 | 8/2009 | Kaiser et al. | |
| 2009/0306711 A1 | 12/2009 | Stone et al. | |
| 2009/0312776 A1 | 12/2009 | Kaiser et al. | |
| 2009/0318960 A1 | 12/2009 | Burkhart | |
| 2009/0318961 A1 | 12/2009 | Stone et al. | |
| 2010/0042114 A1 | 2/2010 | Schaffhausen | |
| 2010/0087857 A1 | 4/2010 | Stone et al. | |
| 2010/0145384 A1 | 6/2010 | Stone et al. | |
| 2010/0191342 A1 | 7/2010 | Byrd et al. | |
| 2010/0211075 A1 | 8/2010 | Stone | |
| 2010/0256677 A1 | 10/2010 | Albertorio et al. | |
| 2010/0268273 A1 | 10/2010 | Albertorio et al. | |
| 2010/0268275 A1 | 10/2010 | Stone et al. | |
| 2010/0292792 A1 | 11/2010 | Stone et al. | |
| 2010/0305698 A1 | 12/2010 | Metzger et al. | |
| 2010/0305709 A1 | 12/2010 | Metzger et al. | |
| 2010/0312341 A1 | 12/2010 | Kaiser et al. | |
| 2011/0087284 A1 | 4/2011 | Stone et al. | |
| 2011/0098727 A1 | 4/2011 | Kaiser et al. | |
| 2011/0270278 A1 | 11/2011 | Overes et al. | |

FOREIGN PATENT DOCUMENTS

| | | |
|---|---|---|
| AU | 440266 | 10/1967 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |

| | | |
|---|---|---|
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO 8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2005104992 | 11/2005 |

OTHER PUBLICATIONS

"Panalok Anchor with PDS II and Ethibond Suture", Mitek Products Ethicon, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device.
Arthrotek, A Biomet Company; Sure fire Hybrid Meniscal Device; Launch Date: Fall AANA 2004.
Bio-Intrafix (TCP/PLA & Intrafix, Tibial Soft Tissue Fasteners, by DePuy Mitek, 6 sheets, (date unknown).
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
"Do your next distal tendon repair with . . . The Lubbers Technique", Teno Fix® brochure, 2003 (2 pages) Ortheon® Medical.
"Make your next tendon repair an open-and-shut case. The Teno Fix® Tendon Repair System", Teno Fix® brochure, 2003 (2 pages) Ortheon® Medical.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
Interview Summary mailed Jul. 14, 2011 for U.S. Appl. No. 12/196,407.
Interview Summary mailed Jun. 20, 2011 for U.S. Appl. No. 12/196,405.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Notice of Allowance (Supplemental Notice of Allowability) mailed Apr. 15, 2011 for U.S. Appl. No. 12/196,398, filed Aug. 22, 2008; now U.S. Patent No. 7,959,650.
Notice of Allowance (Supplemental Notice of Allowability) mailed Mar. 9, 2011 for U.S. Appl. No. 12/196,398, filed Aug. 22, 2008; now U.S. Patent No. 7,959,650.
Notice of Allowance mailed Jun. 1, 2009 for U.S. Appl. No. 11/541,506, filed Sep. 29, 2006; now U.S. Patent No. 7,601,165.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398, filed Aug. 22, 2010; now U.S. Patent No. 7,959,650.
Office Action mailed Apr. 11, 2011 for U.S. Appl. No. 12/196,405.
Office Action mailed May 19, 2009 for U.S. Appl. No. 11/541,505, filed Sep. 29, 2006; now U.S. Patent No. 7,658,751.
Office Action mailed May 4, 2011 for U.S. Appl. No. 12/196,407, filed Aug. 22, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Patent No. 7,658,751.
Restriction Requirement mailed Mar. 9, 2009 for U.S. Appl. No. 11/541,506, filed Sep. 29, 2006; now U.S. Patent No. 7,601,165.
Restriction Requirement mailed Sep. 29, 2010 for U.S. Appl. No. 12/196,398, filed Aug. 22, 2008; now U.S. Patent No. 7,959,650.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
US 6,238,418, 05/2001, Schwartz et al. (withdrawn)

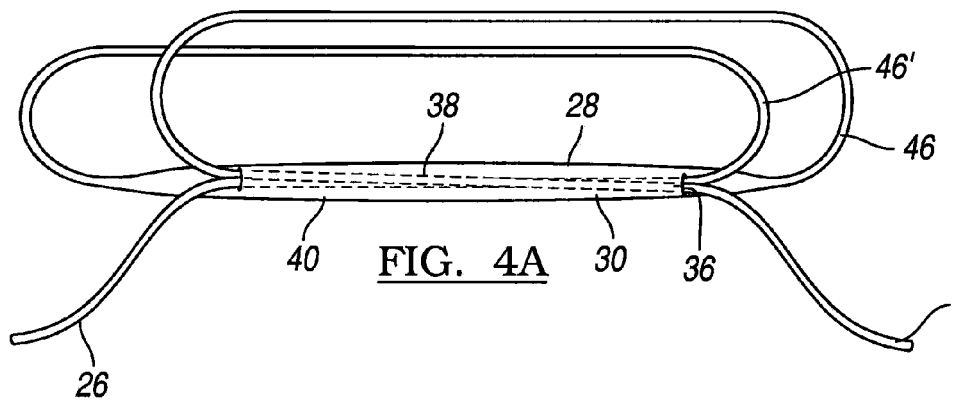
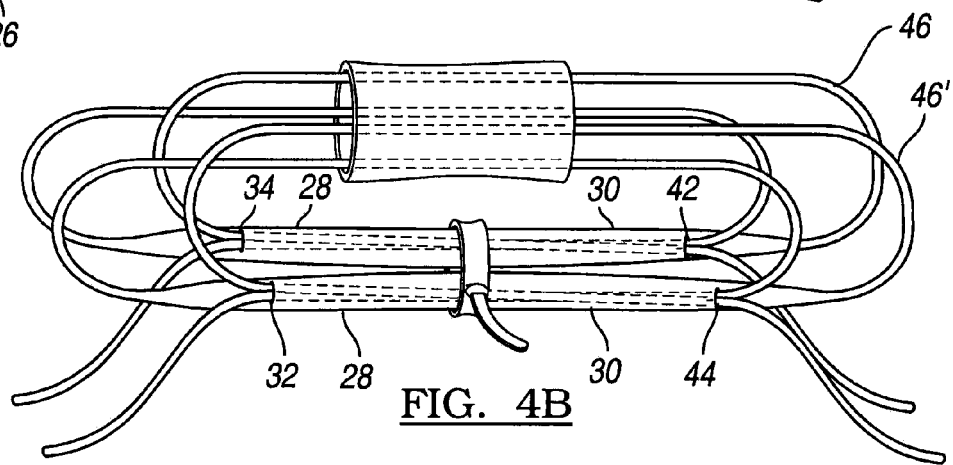
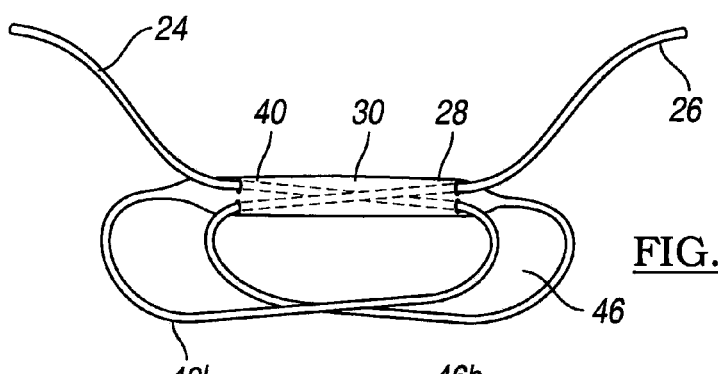
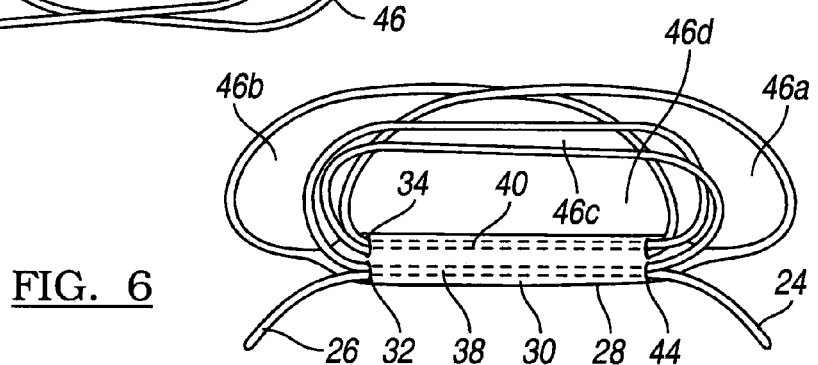

METHOD AND APPARATUS FOR COUPLING SOFT TISSUE TO A BONE

CROSS-REFERENCE TO RELATED APPLICATIONS

This application is a continuation-in-part application of U.S. Pat. No. 7,601,165 issued Oct. 13, 2009 (application Ser. No. 11/541,506 filed on Sep. 29, 2006), and is a continuation-in-part application of U.S. Pat. No. 7,909,851 issued Mar. 22, 2011 (application Ser. No. 12/014,399 filed on Jan. 15, 2008), and is a continuation-in-part application of U.S. Pat. No. 7,905,904 issued Mar. 15, 2011 (application Ser. No. 12/014,340 filed on Jan. 15, 2008), and is a continuation-in-part application of U.S. Pat. No. 7,905,903 issued Mar. 15, 2011 (application Ser. No. 11/935,681 filed on Nov. 6, 2007), and is a continuation-in-part application of U.S. Pat. No. 7,857,830 issued Dec. 28, 2010 (application Ser. No. 11/869,440 filed on Oct. 9, 2007), and is a continuation-in-part application of United States Publication No. 2008/0255613 (Ser. No. 11/784,821 filed on Apr. 10, 2007), and is a continuation-in-part application of U.S. Pat. No. 7,749,250 issued Jul. 6, 2010 (application Ser. No. 11/347,661 filed on Feb. 3, 2006), and is a continuation-in-part application of United States Publication No. 2006/0190042 (Ser. No. 11/347,662 filed on Feb. 3, 2006) now abandoned. The disclosures of the above applications are incorporated herein by reference.

FIELD

The present disclosure relates to method of coupling soft tissue to a bone and, more particularly, to a method of implanting an ACL within a femoral tunnel.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single pre-formed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first end of the suture through a first aperture into a passage defined by the suture and out a second aperture defined by the suture so as to place the first end outside of the passage. A second end of the suture is passed through the second aperture into the passage and out the first aperture so as to place the second end outside of the passage.

A method of surgically implanting a suture construction in a femoral tunnel is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. The first and second ends and the first and second loops are then passed through the femoral tunnel. Soft tissue is then passed through the first and second loops. Tension is applied onto the first and second ends to constrict the first and second loops to pull the soft tissue into the tunnel.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled to at least one of the first and second loops. After the fastener is coupled to the patient, tension is applied onto the first and second ends to constrict at least one of the first and second loops.

In another embodiment a method of surgically implanting a soft tissue replacement for attaching two bone members is disclosed. A first and second tunnel is formed in first and second bones. A locking member having a first profile which allows insertion of the locking member through the tunnel and a second profile which allows engagement with the positive locking surface upon rotation of the locking member is provided. The suture construction described above is coupled to the locking member. The first and second ends and the first and second loops of the construction and the locking member are threaded through the first and second tunnels. Soft tissue is threaded through the first and second loops so as to engage bearing surfaces on the first and second loops. The locking member is then engaged.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 4A and 4B represent alternate suture configurations;

FIGS. 5-7 represent further alternate suture configurations;

DETAILED DESCRIPTION

Figure 1:
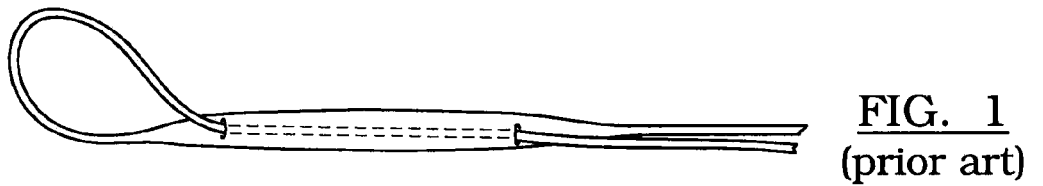
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
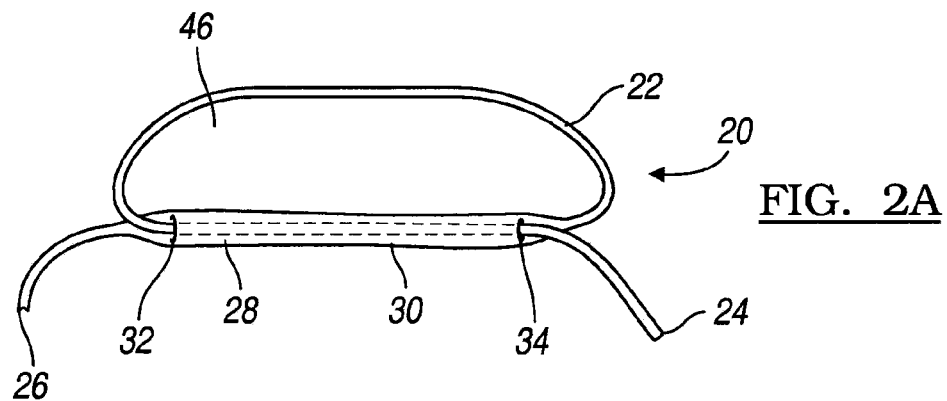
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
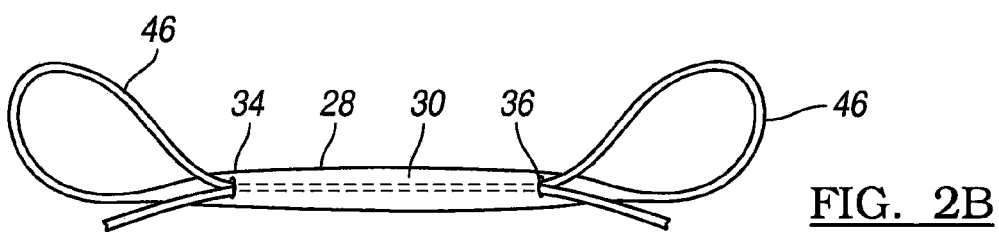
Figure 3:
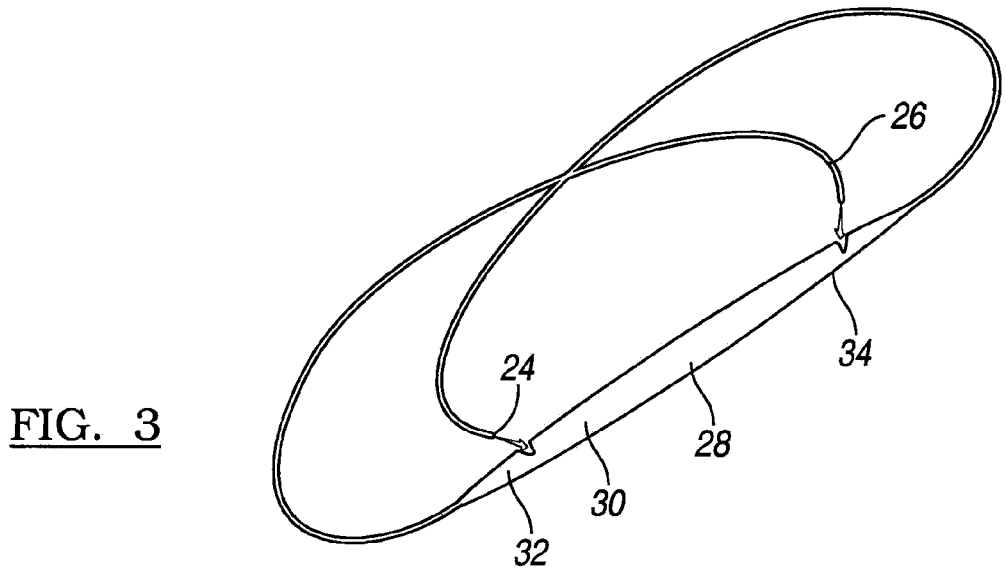
FIG. 3 represents the formation of the suture configuration shown in FIG. 4A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 7:
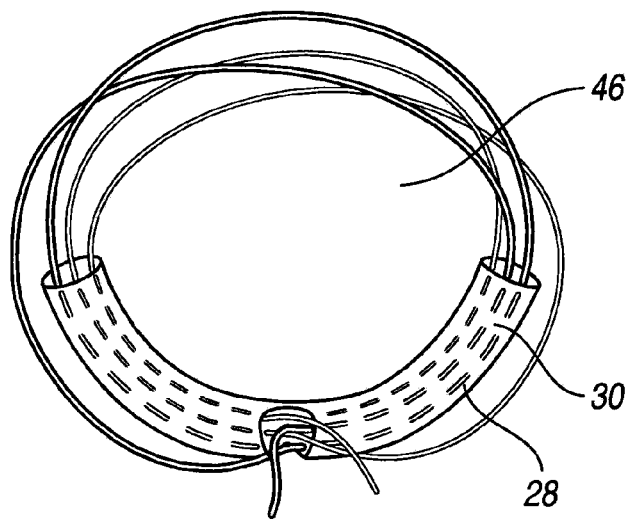
Figure 8:
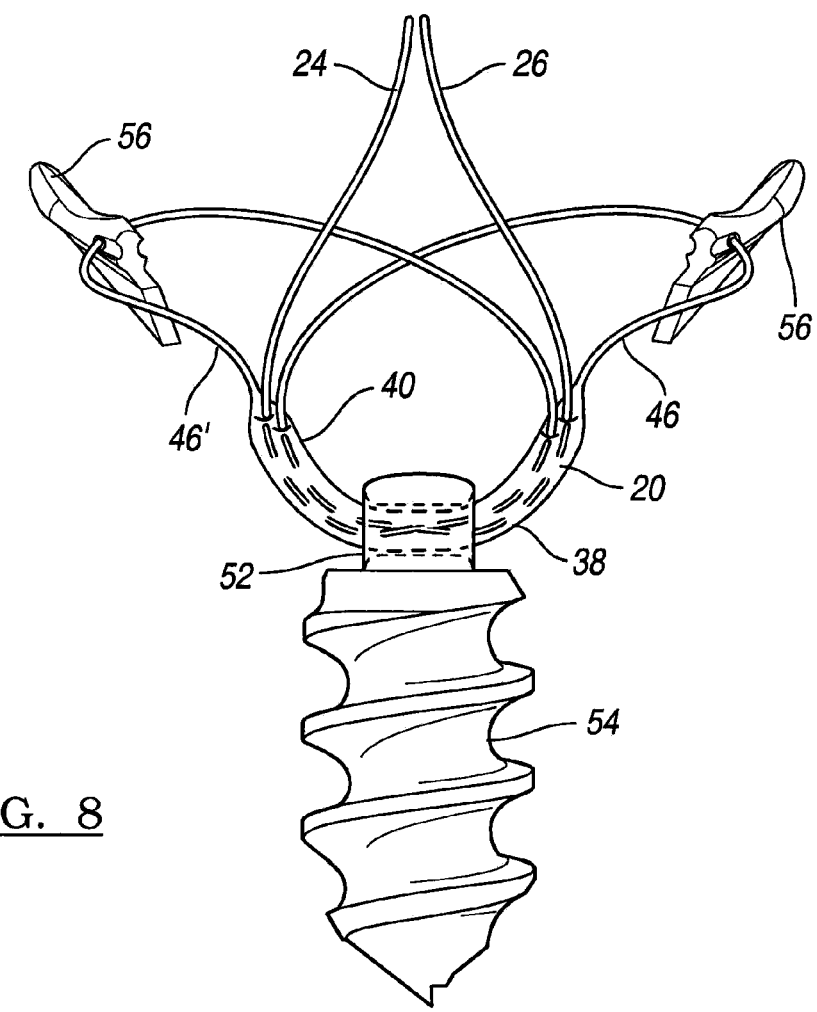
FIG. 8 represents the suture construction according to FIG. 5 coupled to a bone engaging fastener.
Figure 9:
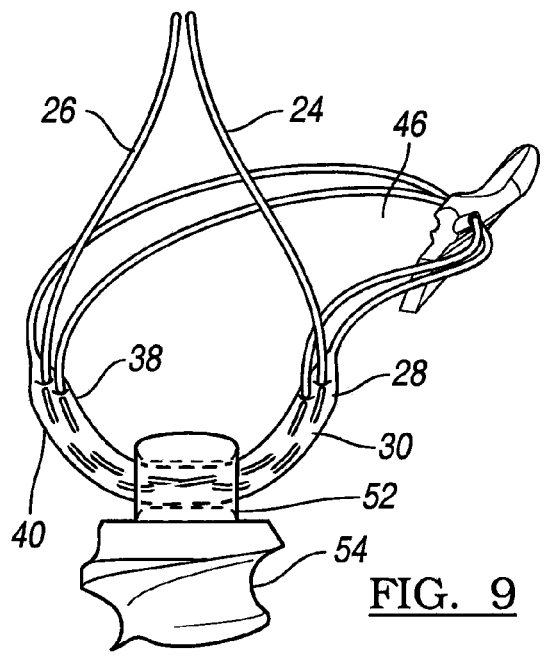
FIGS. 9-11B represent the coupling of the suture construction according to FIG. 5 to a bone screw.
Figure 10:
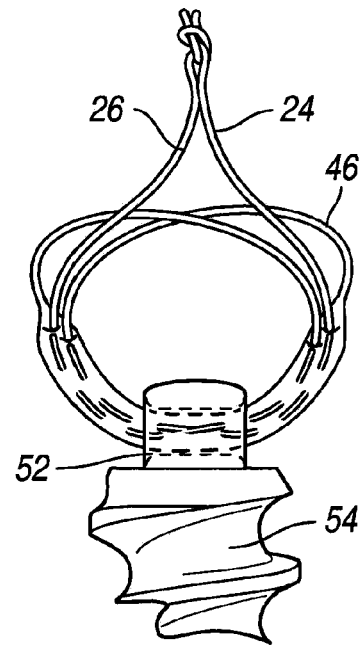

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
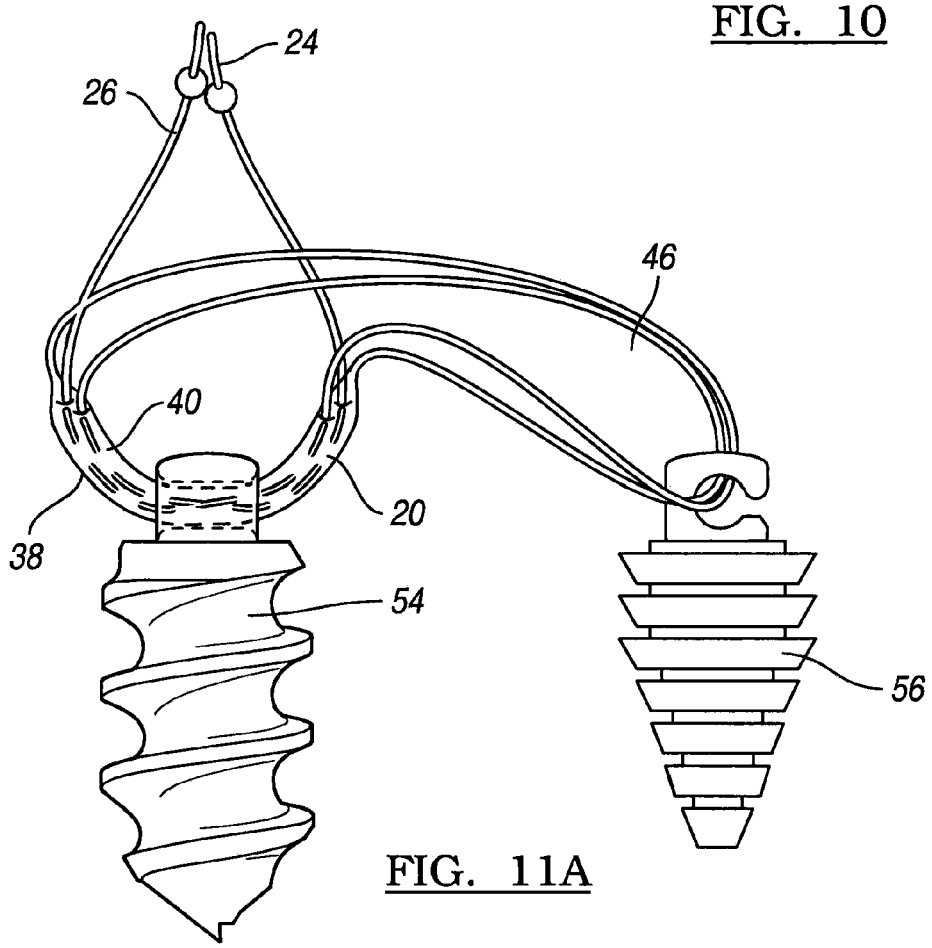
Figure 11B:
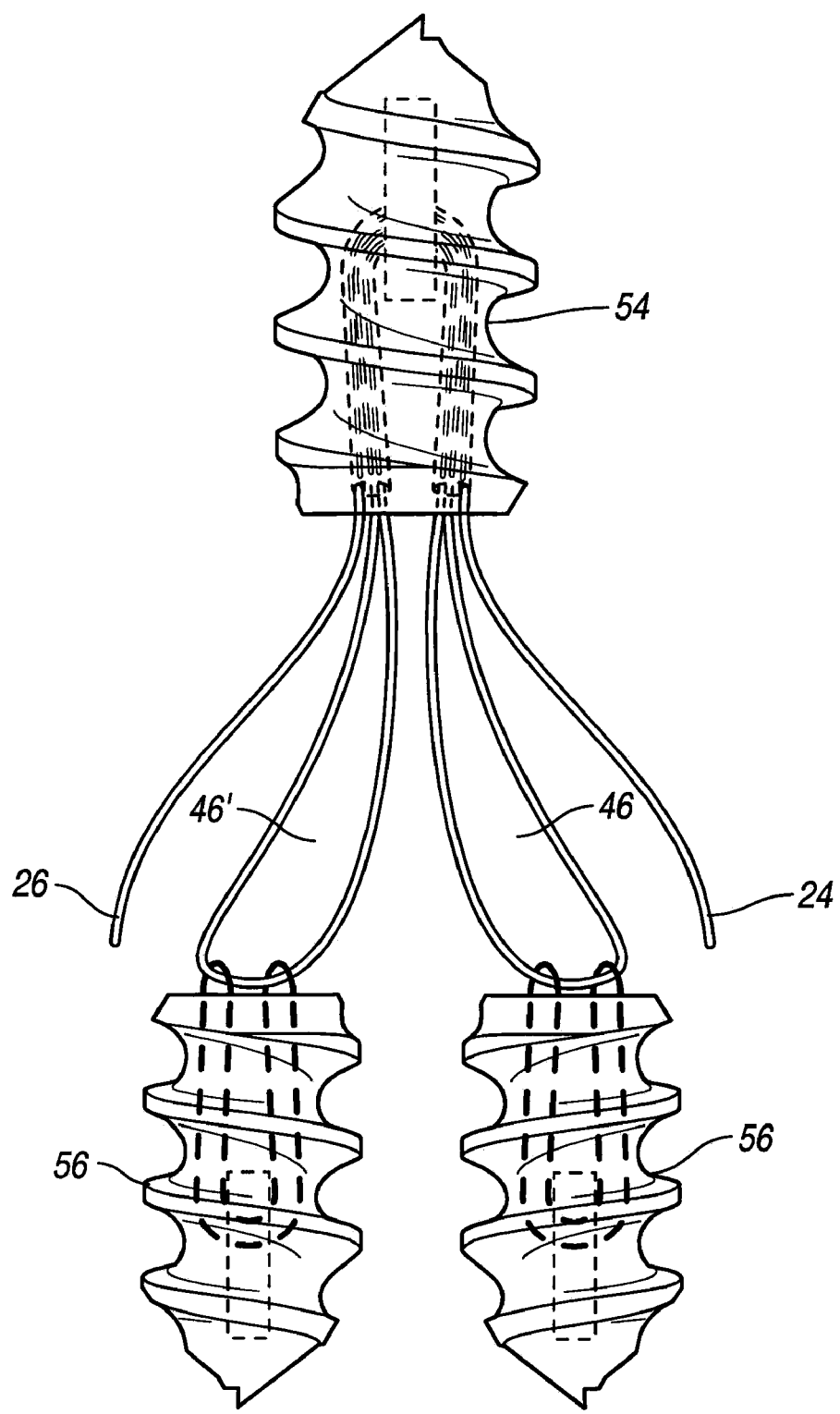

FIG. 11B represents the coupling of the suture construction according to FIG. 2B with a bone fastening member. Coupled to a pair of loops 46 and 46' is tissue fastening members 56. The application of tension to either the first or second end 24 or 26 will tighten the loops 46 or 46' separately.

Figure 12A:
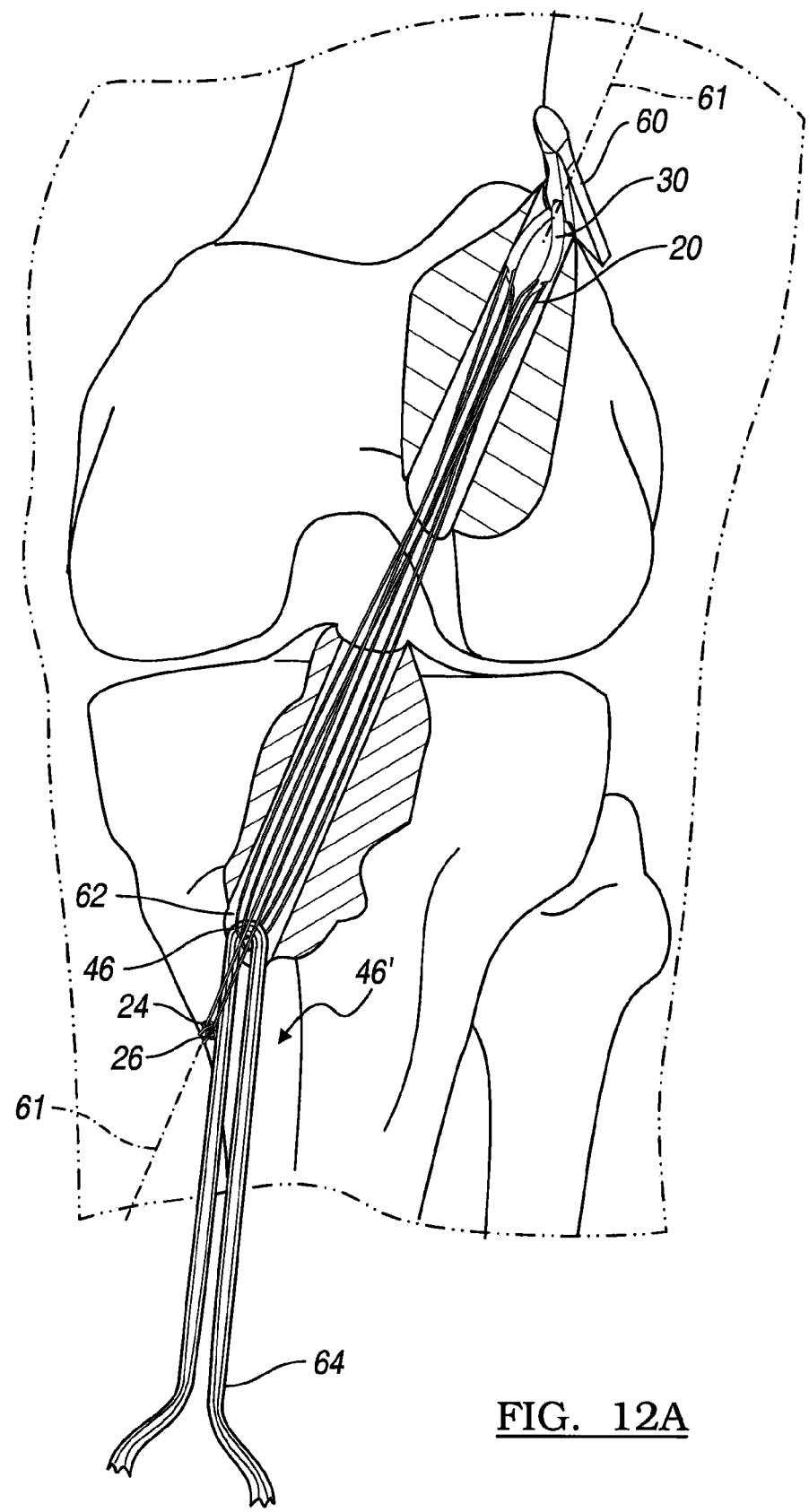
FIGS. 12A-12E represent the coupling of a soft tissue to an ACL replacement in a femoral/humeral reconstruction.
Figure 12B:
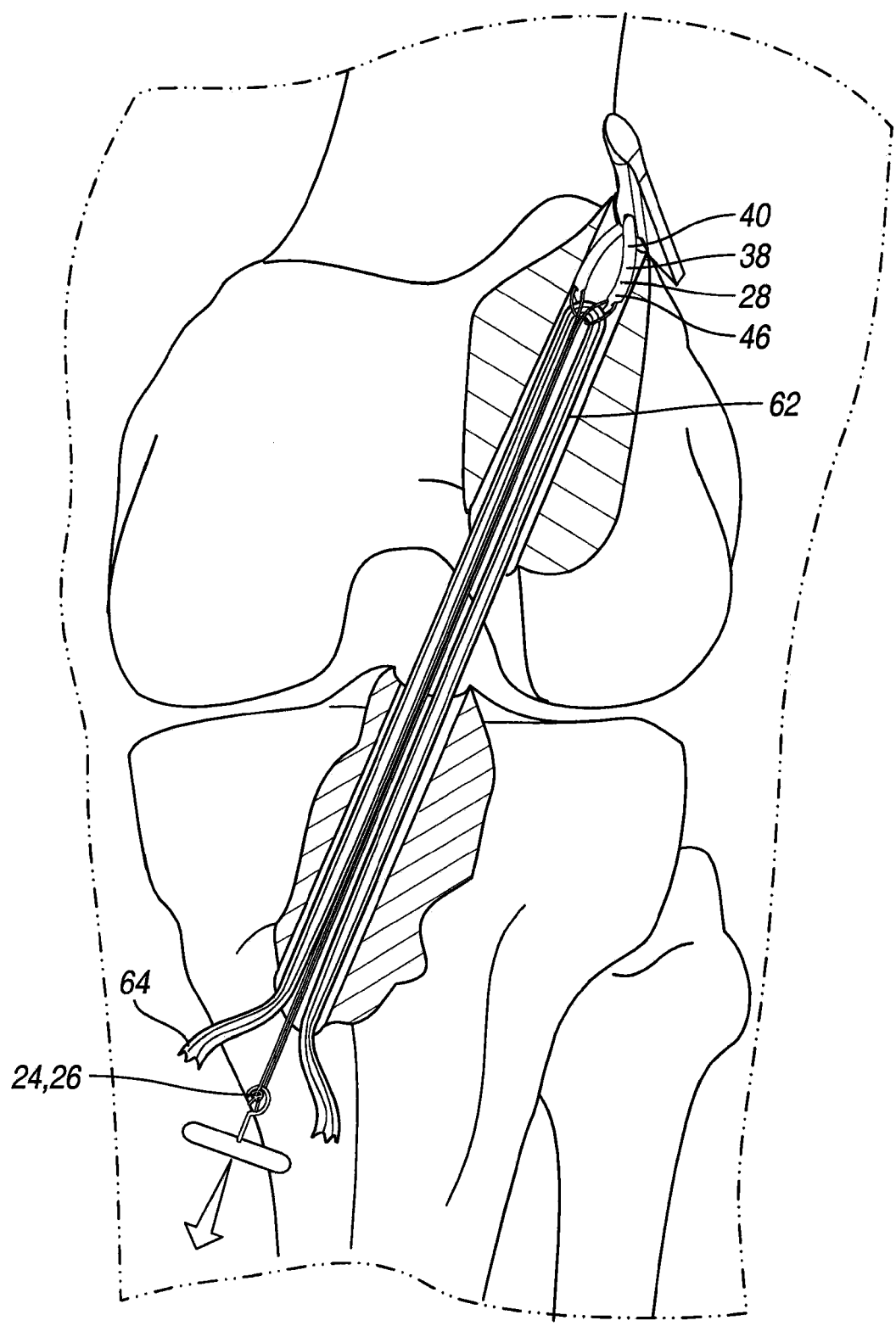

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member 60. The member 60 can have a first profile which allows insertion of the member 60 through the tunnel and a second profile which allows engagement with a positive locking surface upon rotation. The longitudinal passage portion 30 of the suture construction 20, member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the member 60, application of forces to the ends 24, 26 may reduce the seating force applied by the member 60 onto the bone.

Figure 12C:
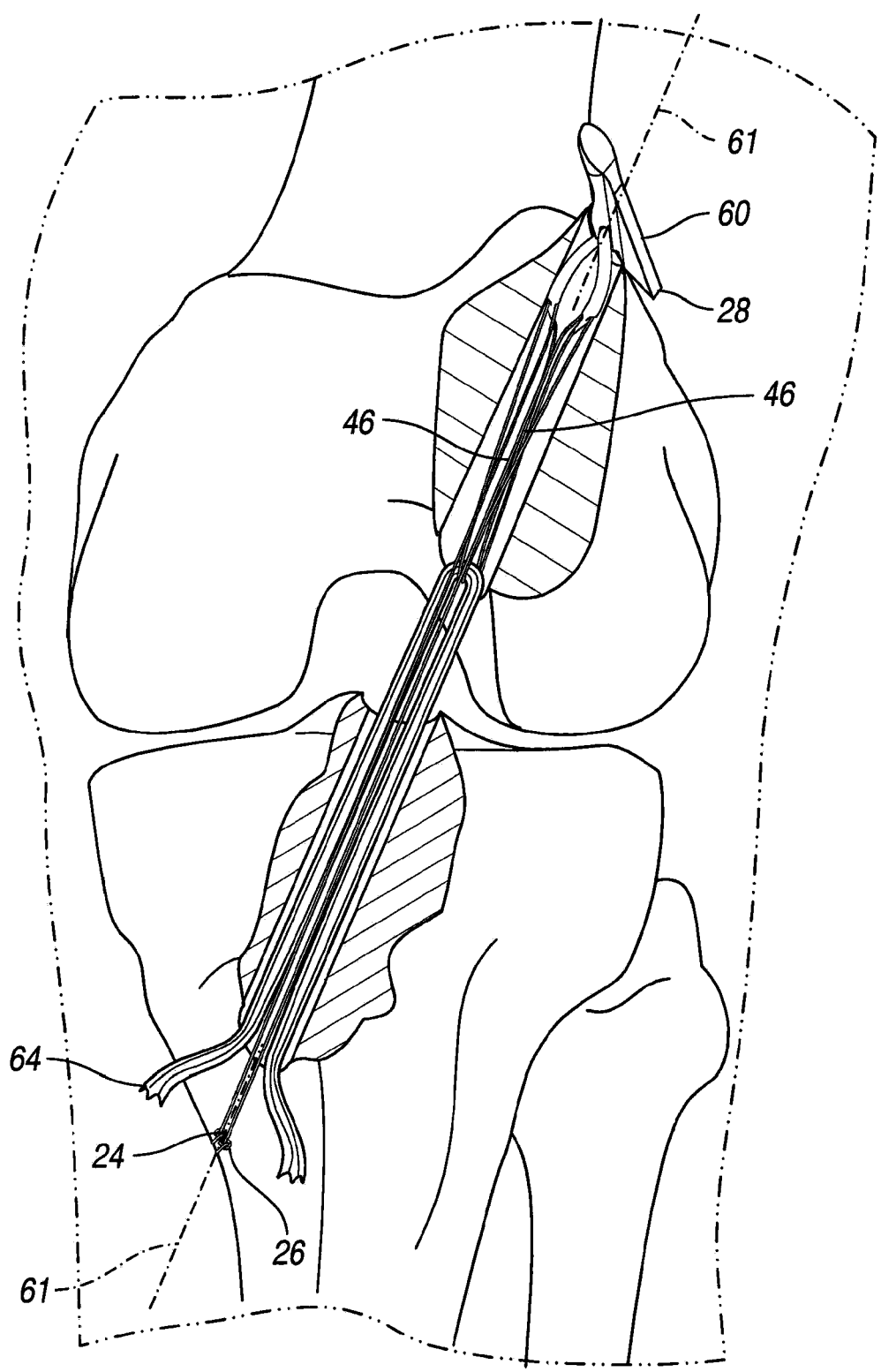
Figure 12D:
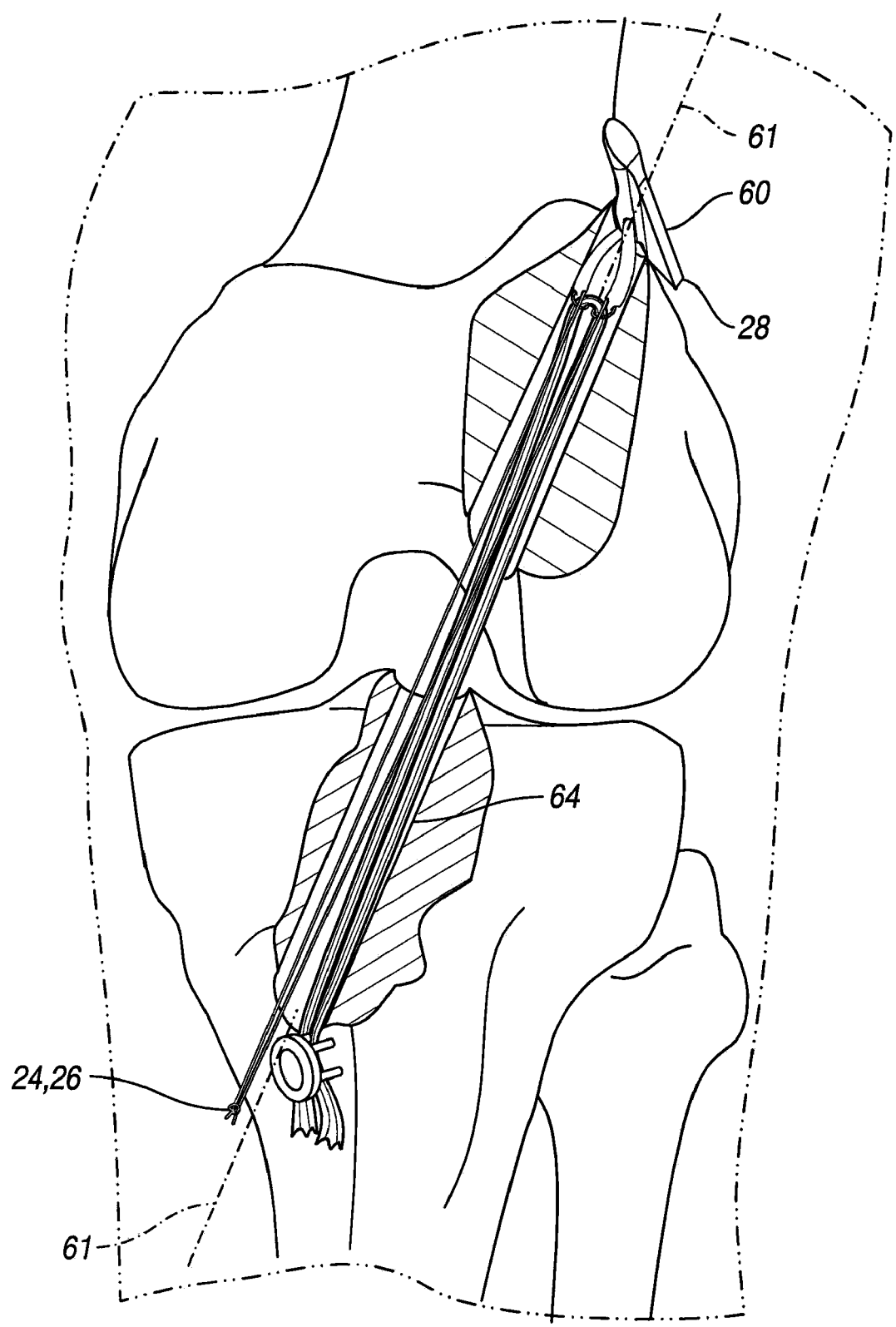

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known. The suture construction has loops 46 and 46' with a first length which allows rotation of the fixation member 60. Application of tension onto the ends 24, 26 of the sutures pulls the fixation member 60 into position and the loops 46 and 46' into a second length. In this position, rotation of the locking member in inhibited.

Figure 12E:
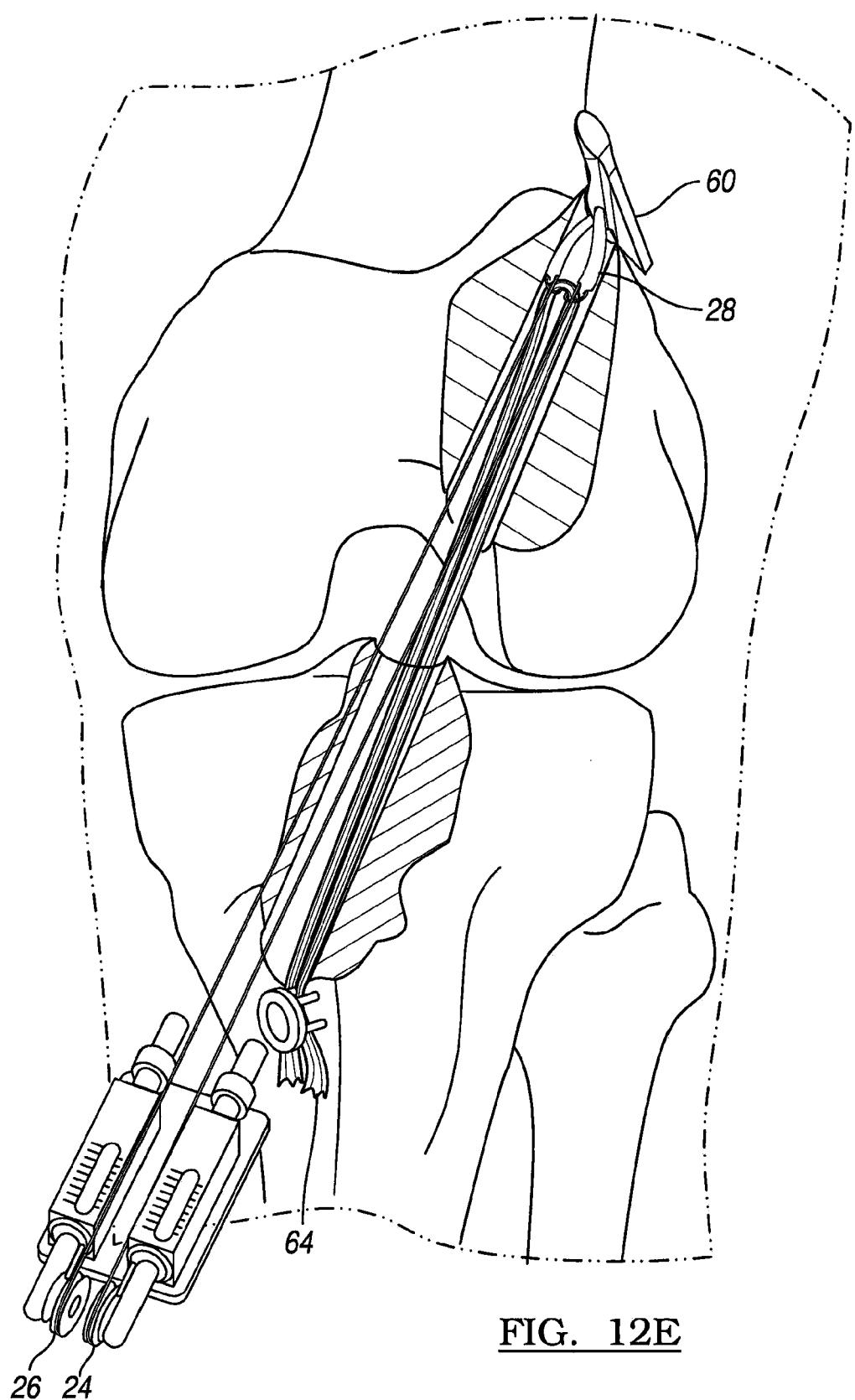
Figure 13A:
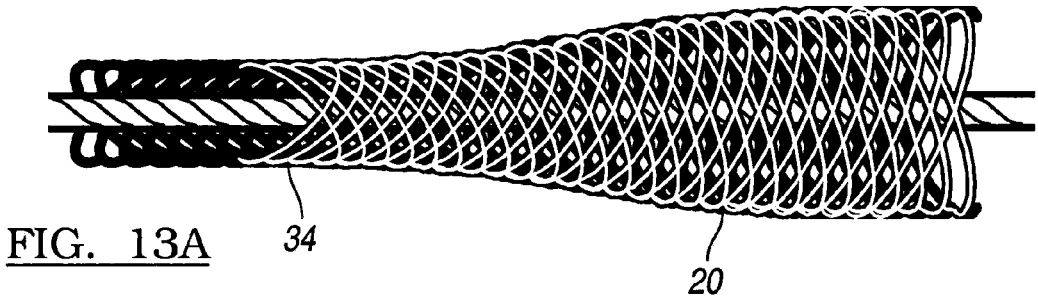
FIGS. 13A-13D represent a close-up view of the suture shown in FIGS. 1-11C.
Figure 13B:
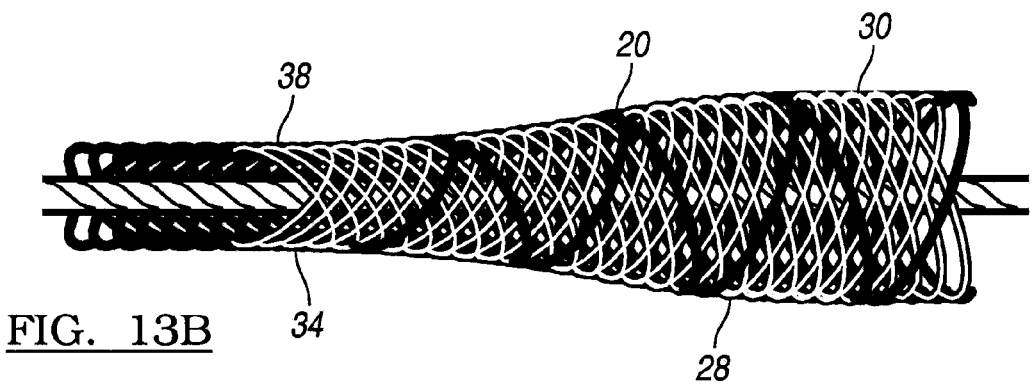
Figure 13C:
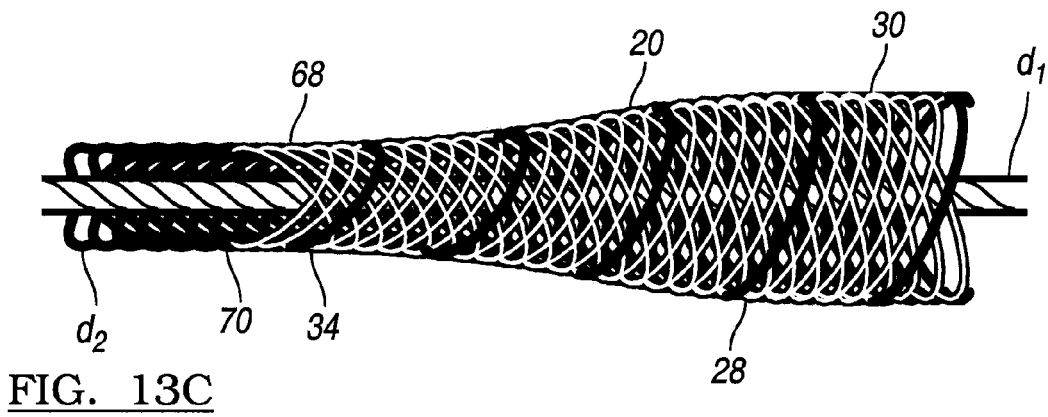
Figure 13D:
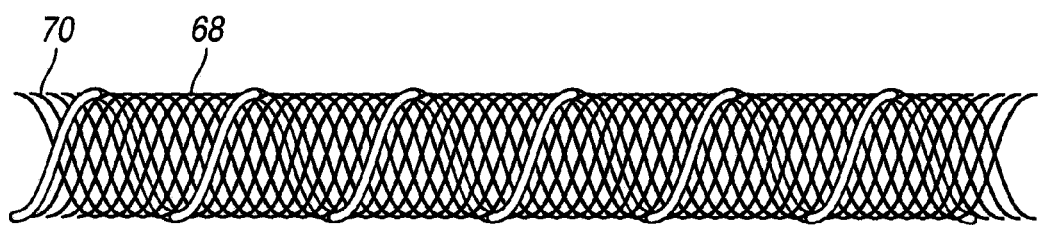

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14:
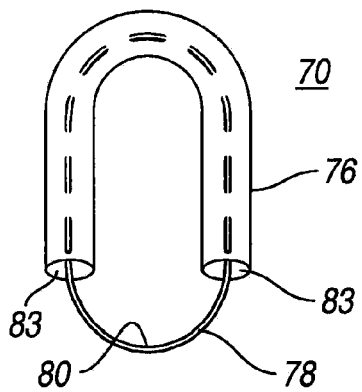
FIGS. 14-16 represent fixed length textile anchors.
Figure 15:
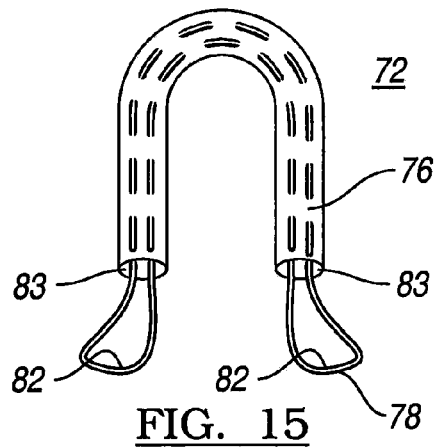
Figure 16:
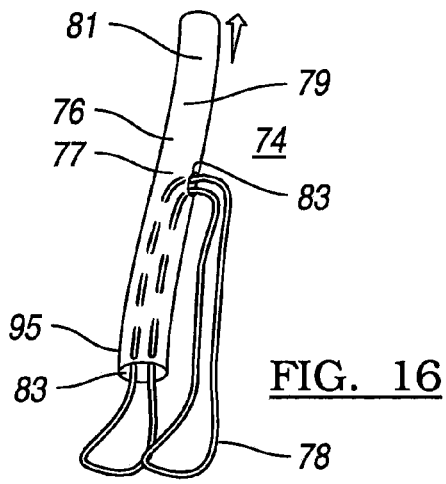

FIGS. 14-16 represent collapsible anchors 70, 72, 74 according to the present teachings. The anchors are deformable from a first cross section to a second engaging cross section. The anchors 70, 72, 74 are biocompatible materials for example polymer or a knit or woven textile such as a braided nylon material. Disposed within a collapsible tube 76 is a closed loop of suture material 78 which may form a portion of the collapsible tube 76. Optionally, this collapsible tube 76 can be slidable with respect to the closed loop of suture material 78. The collapsible tube 76 is further collapsible to form a fabric mass 110 (see for example FIG. 29B).

The suture material 78 can be passed through a pair of openings 83 in the collapsible tube 76 a single time to form a single soft tissue bearing surface 80. Additionally, (see FIG. 15), the closed loop of the suture material 78 can be looped over itself and passed through the collapsible flexible tube 76 to form a pair of soft tissue bearing surface portions 82. In each of the embodiments shown, the collapsible tube 76 defines at least one tube bearing surface.

FIG. 16 represents a closed loop of suture 78 passed through an aperture 77 defined in a body 79 of the collapsible tube 76. In this regard, the suture 78 is passed through a first open end 95 of the tube 78 and through the aperture 77 leaving a portion 81 of the collapsible tube 76 which can be used to assist in the insertion of a graft to a patient (see FIG. 32A).

Figure 17:
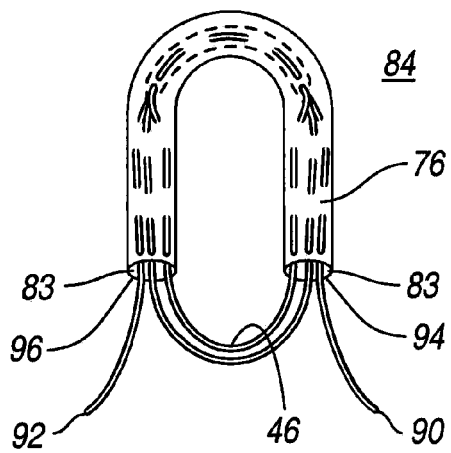
FIGS. 17-21 represent adjustable length textile anchors according to the teachings herein.
Figure 18:
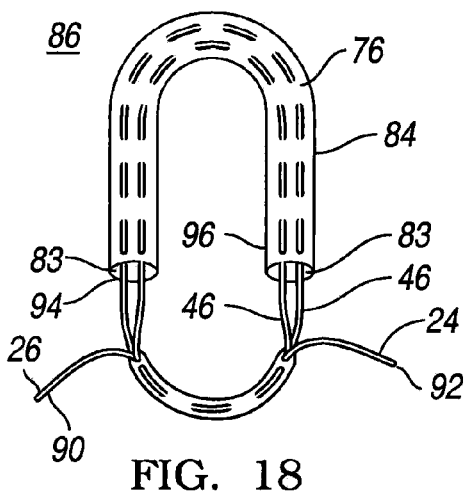
Figure 19:
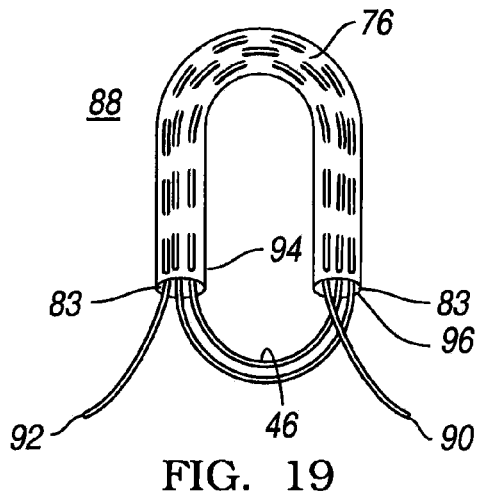

FIGS. 17-19 represent adjustable sized loops of suture material 78 disposed within the collapsible tube 76 so as to form a suture anchor assembly 84, 86, 88. FIG. 17 shows the suture material 78 passed several times through the collapsible tube 76. By applying tension to the ends 90 and 92 of the suture material 78, the loops of the suture material constrict. If placed adjacent to a bearing surface (not shown), the end 94 and 96 of the collapsible tube 76 are brought together, thus collapsing the tube to form a collapsed material or fabric mass 110. It is envisioned a portion of the suture material 78 can be passed through the collapsible tube (75) to help maintain the position of the suture with respect to the collapsible tube 76.

FIGS. 18 and 19 show the loops of the suture construction of FIG. 4a within a collapsible tube 76. The tubular portion of the construction of FIG. 4a can be disposed either within or outside of the collapsible tube 76. As with the embodiment shown in FIGS. 14-16, translation of the tube 76 with respect to the suture material 78 can cause the ends 94 of the tube 76 to be brought together to compress the loops 76 into a fabric mass 110.

Figure 20:
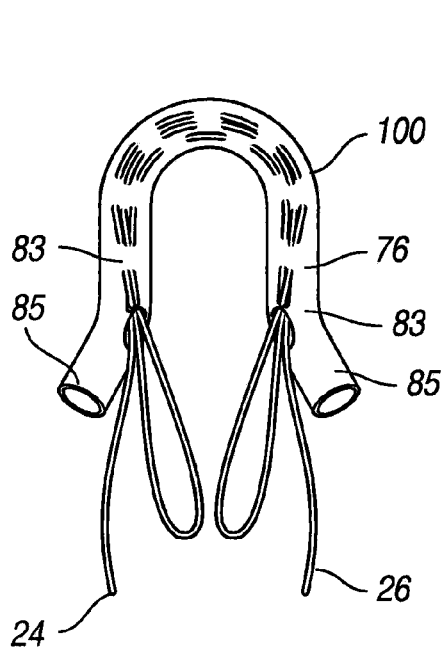
Figure 21:
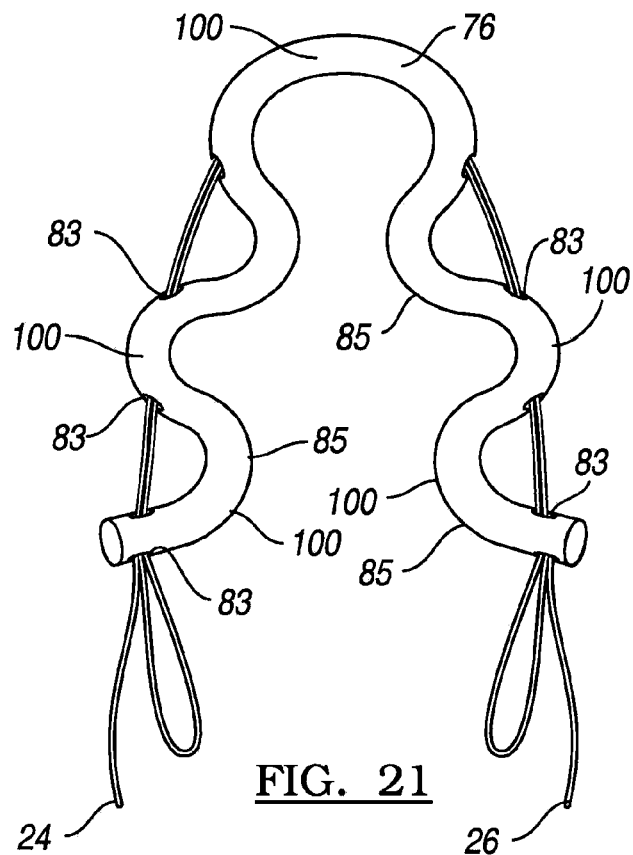

FIGS. 20 and 21 show the loops of FIG. 2B, 4A or 5 disposed within the collapsible tube 76. Shown are the ends and loops disposed at least partially through a portion 100 of the tube 76. Tensioning of the ends 24, 26 causes the portions 100 of the tube 76 to collapse to form a mass 110, while leaving other portions 85 uncollapsed. The outer uncollapsed portion 85 can function as a bearing surface to assist in the collapse of portion 100 when portion 100 is subjected to compressive loads.

Figure 22:
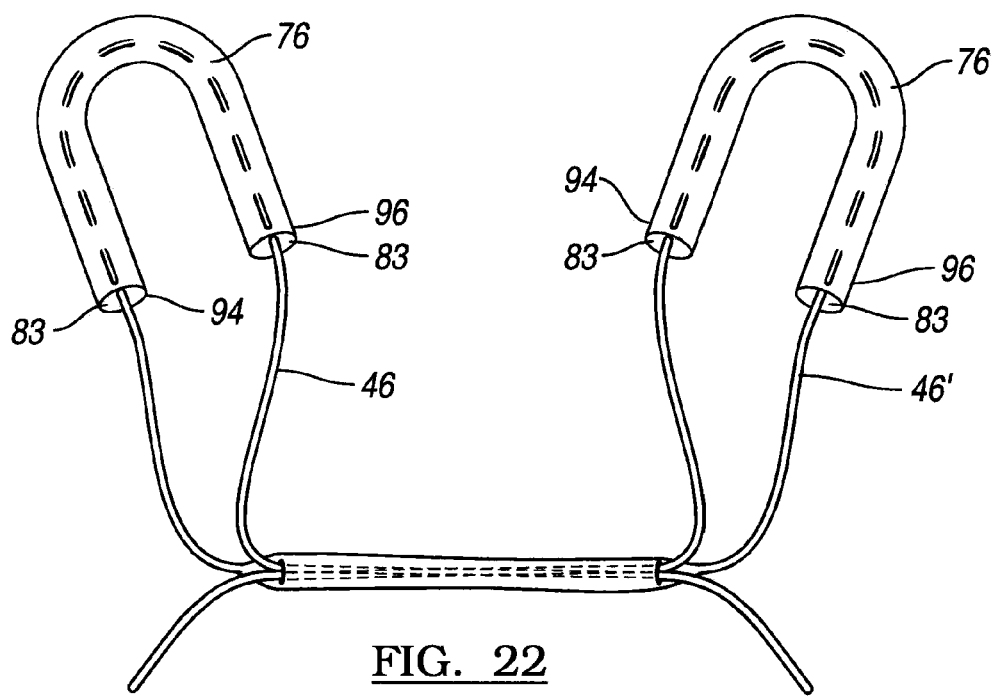
FIGS. 22-24 represent alternate adjustable length textile anchors.

FIG. 21 shows an embodiment where suture loops are passed through the sidewalls of the collapsible tube 76. Optionally, the loops 46 and 47 as well as the ends 24 and 26 can be passed through together. This construction can be used in situations where a large collapsed mass 110 is needed FIG. 22 shows the loop of FIG. 2B having a pair of collapsible tubes 76. The collapsible tubes 76 are disposed about the loops 46 and 46' and will collapse upon application of tension to the ends of the suture construction in a manner which places compressive loads onto the ends of the tube 76. It is envisioned that these collapsible tubes 76 can be collapsed simultaneously or staggered in time as needed by a treating physician. It is also envisioned that the loop construction can be used to pull adjacent portions of a patient's anatomy together.

Figure 23:
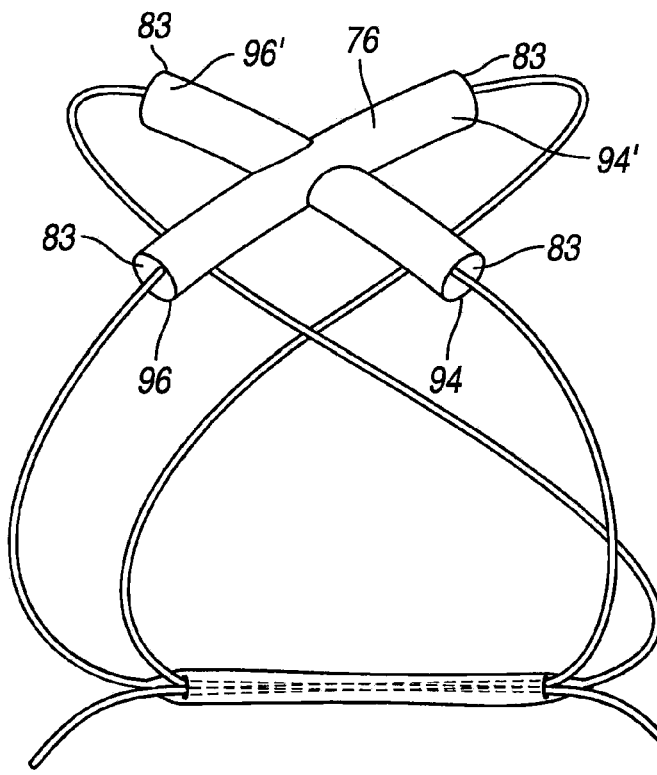

FIG. 23 depicts the loop construction shown in FIG. 2A having its loops disposed through a pair of co-joined crossed collapsible tubes 76. If placed adjacent to a bearing surface, the ends of the co-joined tubes come together, thus increasing in cross-section. This forms the fabric mass 110. This construction can be used in situations where a large collapsed mass is needed.

Figure 24:
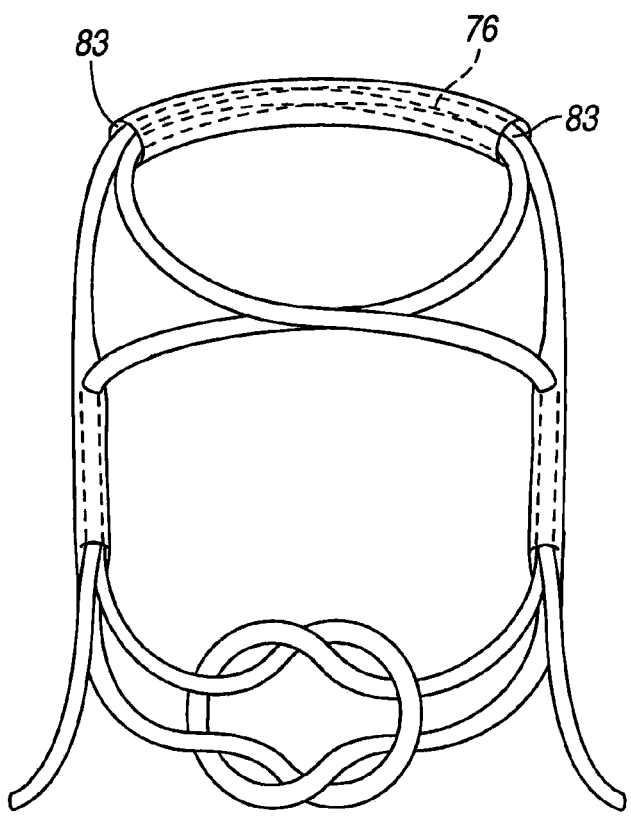

FIG. 24 shows the complex suture construction which embodies a pair of suture constructions of FIG. 2A coupled together using a collapsible tube 76. The ends of the suture 22 can be passed though a pair of passages 30 and 30' formed in the suture material 22. Portions of the suture 22 are looped through each other to form a pair of locked loops 112. This construction can be used to provide a static seat for a graft bearing surface.

Figure 25:
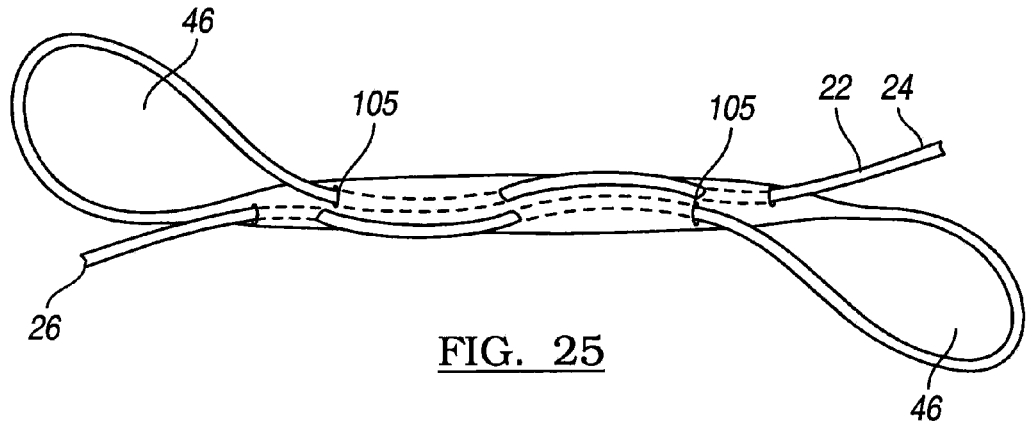
FIGS. 25-27 represent alternate suture configurations.
Figure 26:
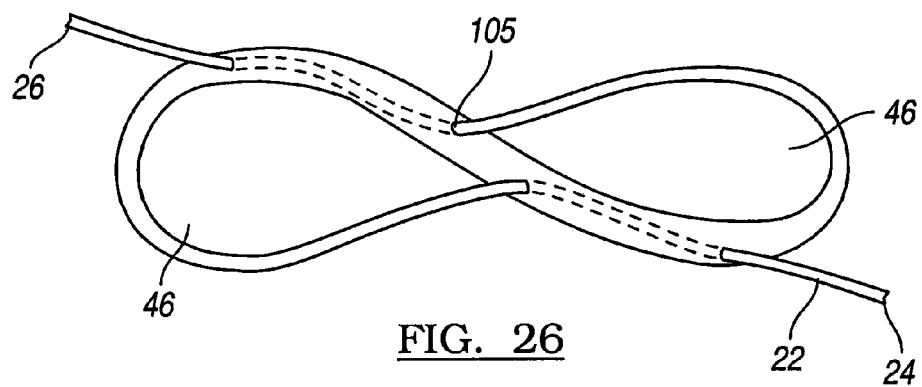
Figure 27:
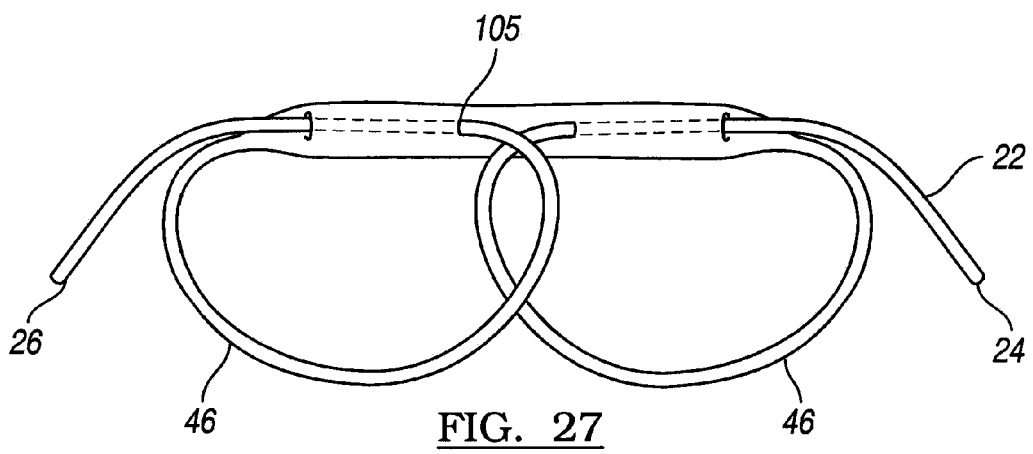

FIGS. 25-27 represent alternate suture constructions where the ends of the sutures 22 are fed multiple times through holes 105 defined within longitudinal passage 30 of the suture to form adjustable loops 46. In situations where relaxation of a tightened construction is to be minimized, the ends can be passed in and out of the passage 30 several times. In this regard, the first and second ends are positioned so as to be parallel and adjacent to each other in the passage 30.

FIGS. 26 and 27 represent constructions where the first and second ends 24 and 26 a passed through the same passage 30, but do not overlap and are not adjacent. This construction may be useful for joining pairs of members. This construction would be useful to bind pairs of appendages such as fingers.

Figure 28:
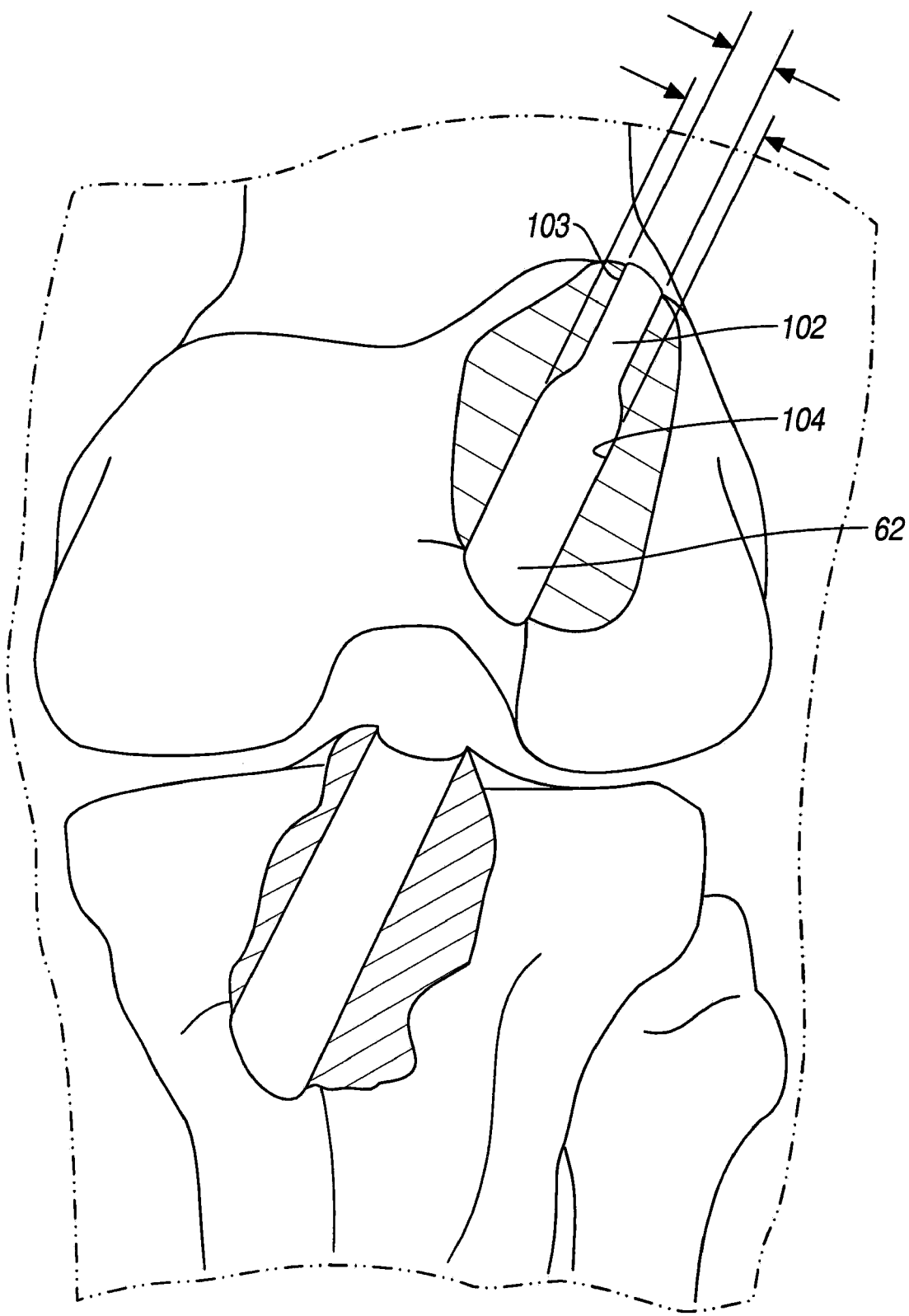
FIG. 28 represents the preparation of the tibia and femur to accept the anchors disclosed in FIGS. 14-24.

FIG. 28 represents the formation of a femoral tunnel shown as a tunnel 62 having a varying diameter. Disposed within either the femoral or tibial tunnel 62 are a first portion 102 having a first diameter and a second portion 104 having a second diameter larger than the first diameter. Defined on an exterior surface of either the tibia or femur is a bearing surface 103, which is configured to interface with the fabric mass 110 of compressed textile material to prevent the relative motion of the fabric mass 110, and thus the suture construction with respect to the bone. This bearing surface can be machined or natural.

Figure 29A:
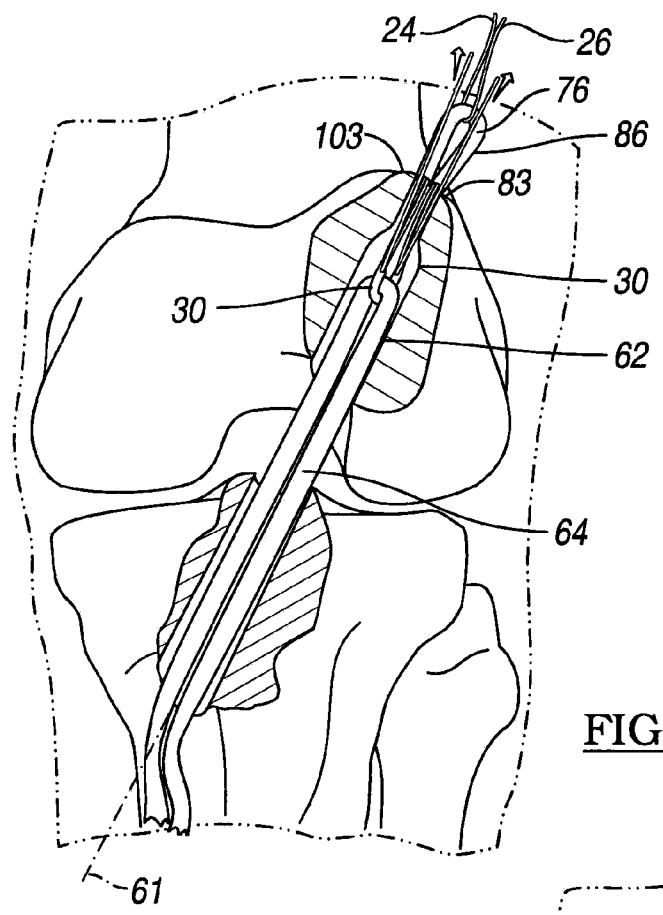
FIGS. 29A and 29B represent the coupling of an ACL replacement in a femoral/tibial reconstruction using the textile anchor of FIG. 18.
Figure 29B:
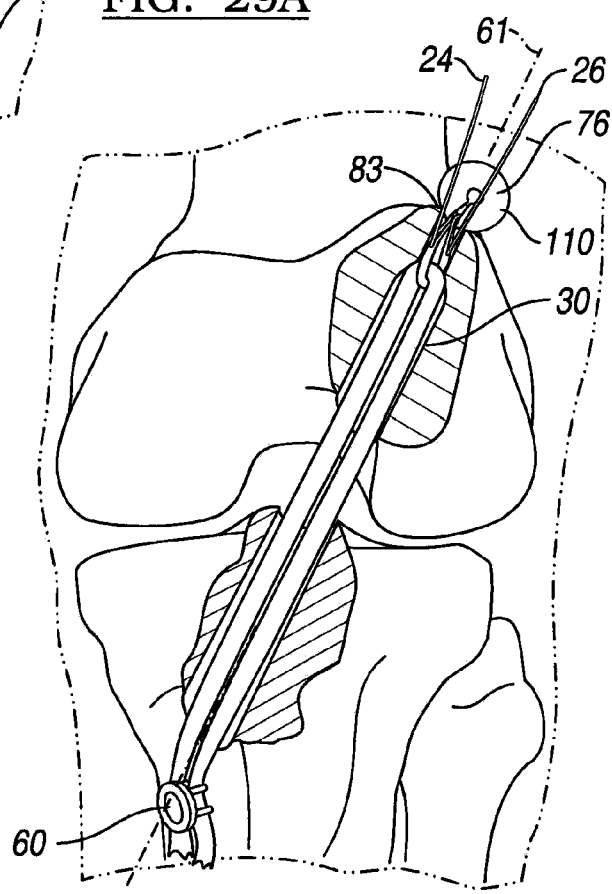

FIGS. 29A and 29B represent potential uses of the suture construction 86 in FIG. 18 in an ACL repair. As can be seen in FIG. 29A, the longitudinal passage portion 30 of suture construction 86 can be first coupled to a collapsible tube 76. The tube 76 can have a first profile which allows insertion of the tube 76 through the tunnel 62 and a second cross-sectional profile which allows engagement with a positive locking surface 103 upon collapse of the collapsible tube 76 into the fabric mass 110. The longitudinal passage portion 30 of the suture construction 84, tube 76, loops 46 and ends 24, 26 can then be pulled through a femoral and tibial tunnel 62. The tube 76 is positioned or coupled to the femur. At this point, a natural or artificial ACL 64 can be passed through a loop or loops 46 formed in the suture construction 20 or can be supported by the passage portion 30. Tensioning of the first and second ends 24 and 26 applies tension to the loops 46 and 47, thus pulling the ACL 64 into the tunnel. In this regard, the first and second ends are pulled through the femoral and tibial tunnel 62, thus constricting the loops 46 about the ACL 64.

After feeding the ACL 64 through the loops 46, tensioning of the ends allows engagement of the ACL with bearing surfaces defined on the loops. The tensioning pulls the ACL 64 through a femoral and tibial tunnel and collapses the tube 76 to form a locking fabric mass 110 outside the bone or tunnel 62. The ACL 64 could be further coupled to the femur or tibia using a transverse pin or plug. As shown in FIG. 29B, once the ACL is fastened to the tibia, further tensioning can be applied to the first and second ends 24, 26 placing a desired predetermined load on the ACL. As described above, this tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62. The longitudinal passage 30 resists relaxation or reverse movement of the suture.

As best seen in FIG. 29B, the body portion 28 and parallel portions 38, 40 of the suture construction 86 remain disposed within the femoral tunnel 62. Further tension of the first ends draws the ACL 64 up through the tibial component into the femoral component. In this way, suture ends can be used to apply appropriate tension onto the ACL 64 component. The ACL 64 would be fixed to the tibial component using a plug or screw either before or after the application of the tension to the suture 22. Additionally, tension can be set on the ACL 64 after the collapsible tube 76 has been compressed.

Figures 30A, 30B:
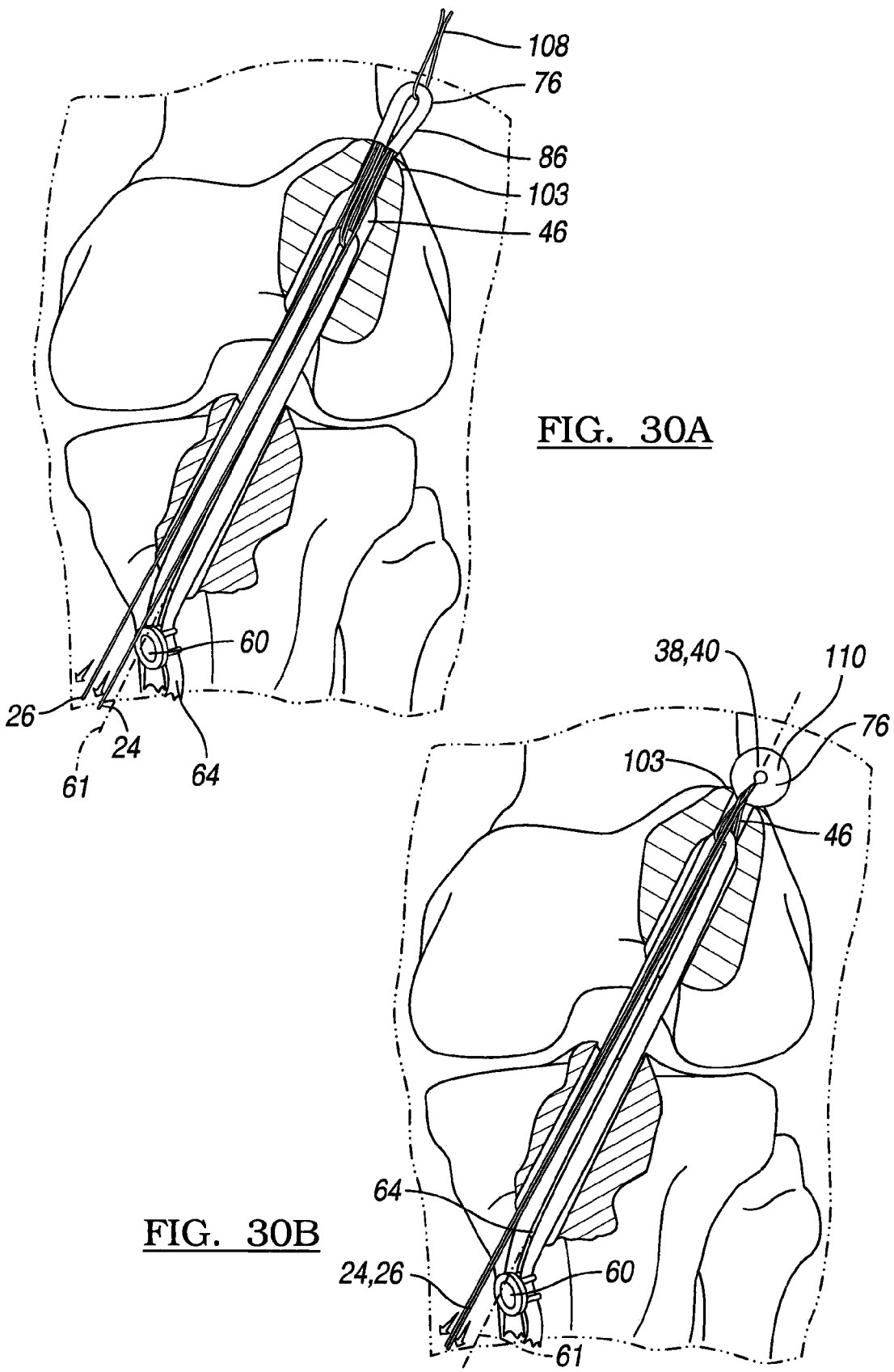
FIGS. 30A and 30B represent the coupling of an ACL replacement in a femoral/tibial reconstruction using the textile anchor of FIG. 17.

FIGS. 30A and 30B represent potential uses of the suture constructions 84 in FIG. 17 in an ACL repair. As can be seen in FIG. 30A, the longitudinal passage portion 30 of suture construction 86 can be first disposed within the tube 76. The tube 76 has a first profile which allows insertion of the tube 76 through the tunnel and a second collapsed profile which allows engagement with a positive locking surface 103. The collapsible tube 76 of the suture construction 84, member 60, and loops 46, 47 can then be passed through a femoral and tibial tunnel 62 using a suture 108. The tube 76 is positioned or coupled to the femur. At this point, a natural or artificial ACL 64 can be passed through a loop or loops 46, 47 formed in the suture construction 84. Tensioning of the first and second ends 24 and 26 applies tension to the loops 46, 47 thus pulling the ACL 64 into the tunnel. In this regard, the first and second ends 26 and 24 are pulled through the femoral and tibial tunnel, thus constricting the loops 46 about the ACL 64 (see FIG. 30B) and collapsing the tube 76 to form the anchoring mass 110. Force applied to graft 64 along axis 61 in the distal direction will seat tube 76 and form anchoring mass 110.

As shown, by holding the suture construction in place 108, the suture construction 84 allows for the application of force along an axis 61 defining the femoral tunnel 62. Specifically, the orientation of the suture construction 84 and, more specifically, the orientation of the longitudinal passage portion 30, the loops 46, and ends 24, 26 allow for tension to be applied to the construction 86 without applying non-seating forces to the tube 76. As an example, should the loops 24, 26 be positioned at the tube 76, application of forces to the ends 24, 26 may reduce the seating force applied by the tube 76 onto the bone.

As best seen in FIG. 30B, the loop portions 46, 47 of the suture construction 84 remain disposed within to the tunnel 62. Further tension of the first ends draws the ACL 64 up through the tibial component into the femoral component. In this way, suture ends can be used to apply appropriate tension onto the ACL 64 component. The ACL 64 would be fixed to the tibial component using a plug or screw 60 adjacent the suture construction 84, as is known.

Alternatively, as shown in FIG. 30B, once the ACL is fastened to the tibia, further tensioning can be applied to the first and second ends 24, 26 placing a desired predetermined load on the ACL. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

Figures 31A, 31B:
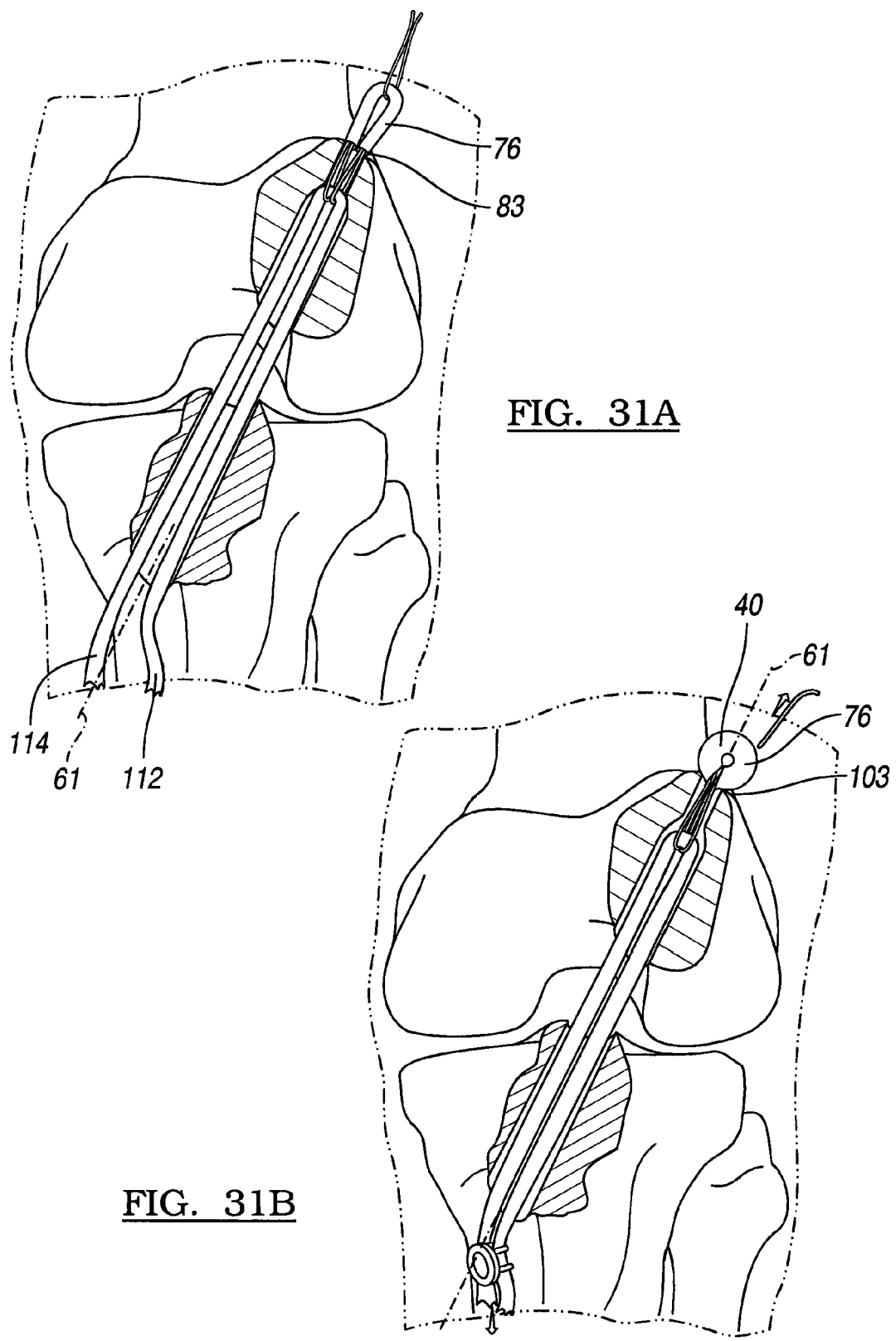
FIGS. 31A and 31B represent the coupling of an ACL replacement in the femoral/tibial reconstruction using the textile anchor of FIG. 15.

FIGS. 31A and 31B represent potential uses of the suture construction 70 in FIG. 14 in an ACL repair. The suture material 78 of suture construction 70 can be first coupled to a collapsible tube 76. The collapsible tube 76 can have a first profile which allows insertion of the construction 70 through the tunnel and a second profile which allows engagement with a positive locking surface 103 upon its compression. Prior to attachment to the femur, a natural or artificial ACL 64 can be passed through a loop or loops 46 formed in the suture material 78. Suture construction 70 can then be passed through a femoral and tibial tunnel 62. The tube 76 is positioned or coupled to the femur. Tensioning of the first and second ends 112 and 114 of the soft tissue applies tension to the loop 76, thus collapsing the tube 76 to form the fabric mass 110. Tension can be applied to the soft tissue which can then be fastened to the tibia using a fastener 60.

Figure 32A:
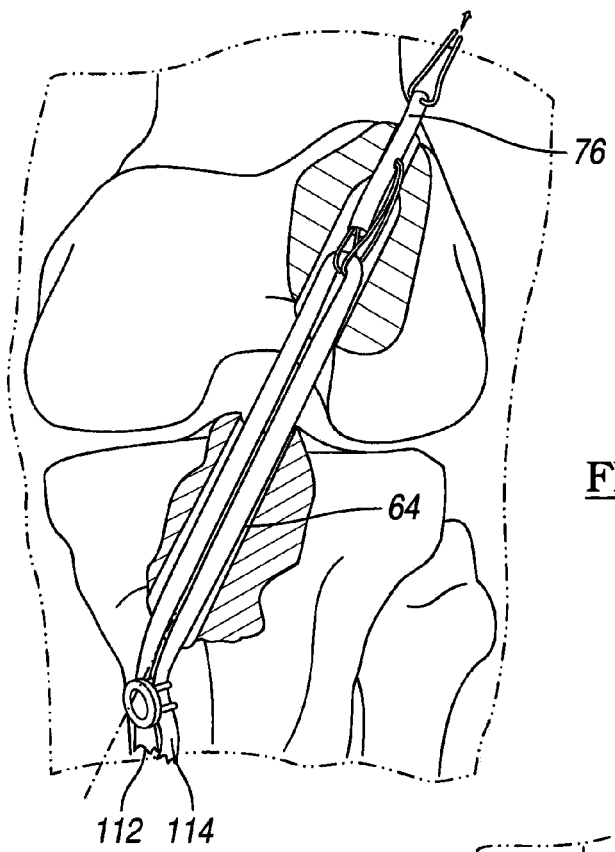
FIGS. 32A and 32B represent the coupling of an ACL replacement in a femoral/humeral reconstruction using the textile anchor of FIG. 16.
Figure 32B:
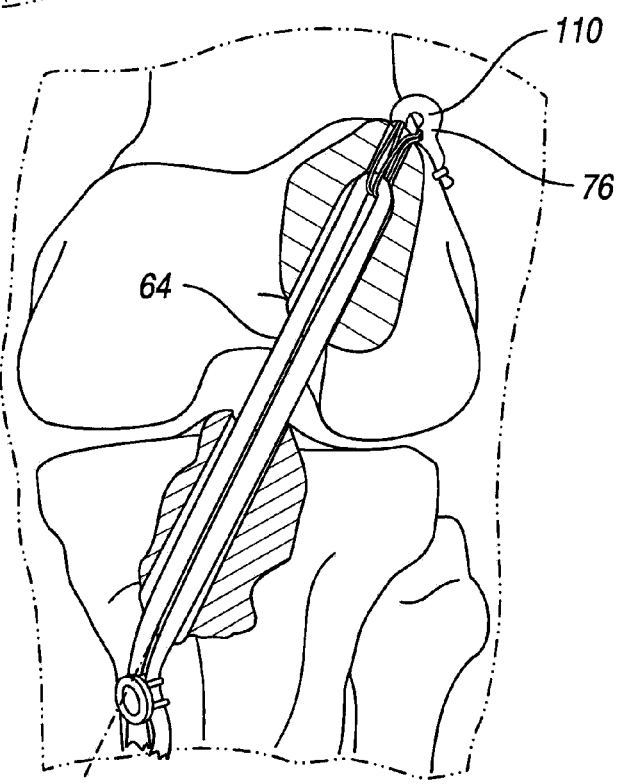

FIGS. 32A and 32B represent potential uses of the suture constructions 74 in FIG. 16 in an ACL repair. The loop of suture 78 is coupled to a collapsible tube 76. The construction 74 can have a first profile which allows insertion of the tube 76 through the tunnel and a second profile which allows engagement with a positive locking surface upon compression. The suture portion 78 of the suture construction 74, tube 76, and soft tissue 64 can then be passed through a femoral and tibial tunnel 62. The tube 76 is positioned or coupled to the femur 103 and collapsed by the application of tension to the soft tissue 64.

As best seen in FIG. 32B, the anchoring mass 110 of the suture construction 72 remains disposed outside the femoral tunnel. Tension is applied to the ends of the ACL 64 up through the tibial component into the femoral component. In this way, ends of the ACL 112, 114 can be used to apply appropriate tension onto the ACL 64 component. The ACL 64 would be fixed to the tibial component using a plug or screw as is known.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Such variations are not to be regarded as a departure from the spirit and scope of the invention.

What is claimed is:

1. A method of surgically implanting a suture comprising:
   forming a bore in a bone;
   said suture having a passage portion defining a through passage;
   passing a first end of the suture through a first aperture defined by the suture into the through passage of the passage portion defined by the suture and out a second aperture defined by the suture so as to place the first end outside of the passage portion and form a first suture loop;
   passing a second end of the suture through a third aperture into the through passage of the passage portion and out a fourth aperture so as to place the second end outside of the passage portion and form a second suture loop, and applying tension to the first and second ends;
   coupling a collapsible tube to the suture;
   passing the collapsible tube through a first opening of the bore such that the collapsible tube is positioned at an outer surface of the bone adjacent to a second opposite opening of the bore; and
   applying a tensile load to a portion of the suture to form an anchoring mass with the collapsible tube having a locking profile engaging the outer surface of the bone, wherein applying the tensile load collapses the collapsible tube from a first profile to a second profile having a larger diameter to form the anchoring mass.

2. The method of surgically implanting a suture according to claim 1 wherein forming a bore in a bone includes forming a femoral tunnel in a femur and forming a tibial tunnel in a tibia.

3. The method according to claim 2 further comprising:
   threading the collapsible tube through at least the femoral tunnel;
   threading a soft tissue through the first suture loop; and
   applying tension onto the suture to apply a load to the soft tissue.

4. The method according to claim 3 wherein applying tension onto the suture includes drawing the soft tissue into one of the femoral or tibial tunnel.

5. The method according to claim 3, wherein applying a tensile load to a portion of the suture to form an anchoring mass with the collapsible tube having a locking profile includes applying tension to the suture to reduce a size of the first suture loop and collapse the collapsible tube about the second surface adjacent the femoral tunnel to secure the suture relative to the femoral tunnel.

6. The method according to claim 5, further comprising coupling a second fastener to the soft tissue to secure the soft tissue relative to the tibial tunnel.

7. The method according to claim 6, wherein applying tension onto the suture to apply the load to the soft tissue includes applying tension onto the suture to reduce a size of the first adjustable suture loop and apply a tensile load to the soft tissue relative to the femur and the tibia.

8. The method according to claim 1 wherein applying tension onto the suture applies a compressive load onto the collapsible tube.

9. The method according to claim 1 further comprising sliding the suture with respect to the collapsible tube.

10. The method according to claim 1 wherein applying tension onto the first and second ends to constrict at least one of the first and second loops collapses the collapsible tube.

11. The method according to claim 1, wherein the first and fourth apertures are positioned about one end of the passage portion and the second and third apertures are positioned about another opposite end of the passage portion.

12. A method of surgically implanting a suture comprising:
    forming a first tunnel in a first bone;
    forming a second tunnel in a second bone;
    positioning a first anchor together with an adjustable suture construct attached thereto into the first tunnel, wherein the adjustable suture construct has a body defining a longitudinal internal bore and a first end of the suture passes through a first aperture defined by the suture body and into the longitudinal internal bore and out a second aperture defined by the suture body to form a first adjustable loop, and wherein a second end of the suture passes through a third aperture defined by the suture body into the longitudinal internal bore and out a fourth aperture defined by the suture body to form a second adjustable loop;
    coupling soft tissue to the adjustable suture construct;
    positioning a second anchor relative to the second tunnel; and
    tensioning at least one end of the adjustable suture construct to apply tension to the soft tissue relative to the first and second bones.

13. The method according to claim 12, wherein forming a first tunnel in a first bone includes forming a femoral tunnel in a femur, and wherein forming a second tunnel in a second bone includes forming a tibial tunnel in a tibia.

14. The method according to claim 12, wherein positioning the first anchor relative to the first tunnel includes:
passing the first anchor in a first profile through the first tunnel; and
engaging the first anchor in a second profile to a positive locking surface of the first bone adjacent the first tunnel.

15. The method according to claim 14, wherein tensioning at least one end of the adjustable suture construct to apply tension to the soft tissue relative to the first and second bones includes collapsing the first anchor from the first profile to the second profile, the second profile forming an anchoring mass.

16. The method according to claim 14, wherein the first anchor includes a collapsible tube collapsible from the first profile to the second profile to form the anchoring mass.

17. The method according to claim 12, wherein coupling soft tissue to the adjustable suture construct includes coupling the soft tissue to the first and second adjustable loops extending from the adjustable suture construct.

18. The method according to claim 17, wherein the adjustable suture construct includes a passage portion, the passage portion being coupled to the first anchor and allowing portions of the first and second loops to slide relative to the passage portion to adjust a size of the first and second loops.

19. The method according to claim 17, wherein positioning a second anchor relative to the second tunnel includes coupling the second anchor to the soft tissue to secure the soft tissue relative to the second tunnel.

20. The method according to claim 19, wherein tensioning at least one end of the adjustable suture construct to apply tension to the soft tissue relative to the first and second bones includes tensioning at least one end of the adjustable suture construct to reduce a size of the first and second adjustable loops to apply tension to the soft tissue relative to the first and second bones.

21. A method of surgically implanting a suture comprising:
forming a femoral tunnel in a femur;
forming a tibial tunnel in a tibia;
positioning a first anchor relative to the femoral tunnel, the first anchor including an adjustable suture construct extending therefrom, the adjustable suture construct including first and second adjustable loops, wherein the adjustable suture construct has a body defining a longitudinal internal bore and a first end of the suture passes through a first aperture defined by the suture body and into the longitudinal internal bore and out a second aperture defined by the suture body to form the first adjustable loop, and wherein a second end of the suture passes through a third aperture defined by the suture body into the longitudinal internal bore and out a fourth aperture defined by the suture body to form the second adjustable loop;
passing soft tissue into and around the first and second adjustable loops;
positioning a second anchor relative to the tibial tunnel;
positioning the adjustable suture construct between at least a portion of the femur and the tibia; and
tensioning at least one end of the adjustable suture construct to apply tension to the soft tissue relative to the femur and the tibia.

22. The method according to claim 21, wherein positioning a first anchor relative to the femoral tunnel includes:
passing the first anchor in a first profile through the femoral tunnel; and
engaging the first anchor in a second profile to a positive locking surface of the femur adjacent the femoral tunnel.

23. The method according to claim 22, wherein tensioning at least one end of the adjustable suture construct to apply tension to the soft tissue relative to the femur and the tibia includes tensioning at least one end of the adjustable suture construct to reduce a size of the first and second loops and collapse the first anchor from the first profile to the second profile, the second profile forming an anchoring mass relative to the femur.

24. The method according to claim 21, wherein the first anchor includes a collapsible tube collapsible from the first profile to the second profile under tension to form the anchoring mass.

25. The method according to claim 21, wherein the adjustable suture construct includes a passage portion, the passage portion being coupled to the first anchor and allowing portions of the first and second loops to slide relative to the passage portion to adjust a size of the first and second loops.

26. The method according to claim 21, wherein positioning a second anchor relative to the tibial tunnel includes coupling the second anchor to the soft tissue to secure the soft tissue to the tibial tunnel; and
wherein tensioning at least one end of the adjustable suture construct to apply tension to the soft tissue relative to the femur and the tibia includes tensioning first and second ends of the adjustable suture construct to reduce a size of the first and second adjustable loops to apply tension to the soft tissue relative to the femur and the tibia via the respective first and second anchors.

27. The method according to claim 21, wherein tensioning at least one end of the adjustable suture construct to apply tension to the soft tissue relative to the femur and the tibia includes tensioning first and second ends of the adjustable suture construct to reduce a size of the first and second adjustable loops, which includes sliding the first and second loops relative to the soft tissue coupled thereto.

28. A method of surgically implanting a suture comprising:
forming a femoral bore in a femur and a tibial bore in a tibia;
passing a graft over at least a portion of first and second adjustable loops of an adjustable suture construct, wherein the adjustable suture construct has a body defining a longitudinal internal bore and a first end of the suture passes through a first aperture defined by the suture body and into the longitudinal internal bore and out a second aperture defined by the suture body to form the first adjustable loop, and wherein a second end of the suture passes through a third aperture defined by the suture body into the longitudinal internal bore and out a fourth aperture defined by the suture body to form the second adjustable loop;
passing a first anchor member into the femoral bore, the first anchor member coupled to the adjustable suture construct carrying the graft;
positioning a second anchor member relative to the tibial tunnel; and
tensioning at least one end of the adjustable suture construct to apply tension to the graft relative to the femoral and tibial bores.

29. The method according to claim 28, wherein passing a first anchor member into the femoral bore includes:
passing the first anchor member in a first profile through the femoral bore; and
engaging the first anchor member in a second profile to a positive locking surface of the femur adjacent the femoral bore.

* * * * *

UNITED STATES PATENT AND TRADEMARK OFFICE
CERTIFICATE OF CORRECTION

Page 1 of 2

PATENT NO. : 8,118,836 B2
APPLICATION NO. : 12/196410
DATED : February 21, 2012
INVENTOR(S) : Gregory J. Denham et al.

It is certified that error appears in the above-identified patent and that said Letters Patent is hereby corrected as shown below:

Title Page, Item (56) References Cited, U.S. Patent Documents, Page 2, Column 1, Reference 21,
Replace "RE22,867  3/1947 Ogburn" with --RE22,867  4/1947 Dath--

Title Page, Item (56) References Cited, U.S. Patent Documents, Page 2, Column 1, Reference 54,
Replace "RE26,501  12/1968 Kendrick et al." with --RE26,501  12/1968 Himmelstein et al.--

In the Specifications:

Column 3,
Line 65, after "either" delete "a"

Column 5,
Line 29, replace "in inhibited" with --is inhibited--

Column 6,
Line 31, replace "collapsible tube (75)" with --collapsible tube 75--

Column 6,
Line 34, replace "Fig. 4*a*" with --FIG. 4A--

Column 6,
Line 35, replace "Fig. 4*a*" with --FIG. 4A--

Column 6,
Line 54, after "needed" insert --.--

Signed and Sealed this
Seventeenth Day of July, 2012

David J. Kappos
*Director of the United States Patent and Trademark Office*

Column 7,
Line 8, replace "though" with --through--

Column 7,
Line 22, replace "a passed through" with --are passed through--